US012178416B2

(12) United States Patent
Sullivan et al.

(10) Patent No.: US 12,178,416 B2
(45) Date of Patent: Dec. 31, 2024

(54) TISSUE REMOVAL SYSTEM

(71) Applicant: HOLOGIC, INC., Marlborough, MA (US)

(72) Inventors: Roy H. Sullivan, Marlborough, MA (US); Jessica Tina Schenck, Marlborough, MA (US); George Charles Michaels, Marlborough, MA (US)

(73) Assignee: Hologic, Inc., Marlborough, MA (US)

(*) Notice: Subject to any disclaimer, the term of this patent is extended or adjusted under 35 U.S.C. 154(b) by 1042 days.

(21) Appl. No.: 17/133,691

(22) Filed: Dec. 24, 2020

(65) Prior Publication Data
US 2021/0186472 A1 Jun. 24, 2021

Related U.S. Application Data

(63) Continuation of application No. 15/915,409, filed on Mar. 8, 2018, now Pat. No. 10,874,380, which is a
(Continued)

(51) Int. Cl.
A61B 10/02 (2006.01)
A61B 17/22 (2006.01)
A61B 17/42 (2006.01)

(52) U.S. Cl.
CPC ...... *A61B 10/0283* (2013.01); *A61B 10/0275* (2013.01); *A61B 10/0291* (2013.01);
(Continued)

(58) Field of Classification Search
CPC . A61B 10/02; A61B 10/0233; A61B 10/0241; A61B 10/0266; A61B 10/0283;
(Continued)

(56) References Cited

U.S. PATENT DOCUMENTS 5,730,752 A  3/1998 Alden et al.
5,873,886 A * 2/1999 Larsen ............ A61B 17/32002
                                                      606/167
(Continued)

FOREIGN PATENT DOCUMENTS

WO    99/11184      3/1999
WO    01/72230     10/2001
WO   2017087411    5/2017

OTHER PUBLICATIONS

PCT International Search Report and Written Opinion for International Appln. No. PCT/US2016/062080, Applicant Hologic, Inc., forms PCT/ISA/210, 220, and 237, dated Feb. 22, 2017 (12 pages).

*Primary Examiner* — Diane D Yabut
*Assistant Examiner* — Christian D Knauss
(74) *Attorney, Agent, or Firm* — Vista IP Law Group, LLP

(57) ABSTRACT

A tissue removal device includes a housing, an outer tube having a distal portion configured for transcervical insertion into a uterus, an inner tube slidably disposed within the outer tube lumen, a vacuum generation chamber disposed within the housing, a movable piston slidably disposed in the vacuum generation chamber, a collection chamber, a manual actuator moveably coupled to the housing and operatively coupled to the piston, and proximal and distal one-way valves. The outer tube has an outer tube lumen, a tissue in-take opening proximate a distal end thereof, and a proximal end coupled to the housing. The inner tube has an inner tube lumen extending from an open inner tube distal end to an open inner tube proximal end, the open inner tube distal end comprising a cutting edge configured to sever intrauterine tissue extending through the tissue in-take opening in the outer tube.

13 Claims, 14 Drawing Sheets

Related U.S. Application Data continuation of application No. 15/556,599, filed as application No. PCT/US2016/062080 on Nov. 15, 2016, now Pat. No. 9,913,629.

(60) Provisional application No. 62/255,650, filed on Nov. 16, 2015.

(52) U.S. Cl.
CPC .............. *A61B 17/22031* (2013.01); *A61B 2010/0208* (2013.01); *A61B 17/42* (2013.01); *A61B 2017/4216* (2013.01)

(58) Field of Classification Search
CPC .......... A61B 10/0291; A61B 10/04; A61B 2010/0208; A61B 2010/0225; A61B 17/32; A61B 17/32002; A61B 17/42; A61B 2017/32007; A61B 2017/4216; A61B 2017/2902; A61B 2017/2903; A61B 2017/2912; A61B 2017/2913; A61B 2017/2915; A61B 2017/2916; A61B 2017/4225; A61B 17/320758; A61B 17/320783; A61B 2017/320766; A61B 2017/320775; A61B 2017/320791
See application file for complete search history.

(56) References Cited

U.S. PATENT DOCUMENTS

| | | |
|---|---|---|
| 5,906,615 A | 5/1999 | Thompson |
| 6,032,673 A | 3/2000 | Savage et al. |
| 7,226,459 B2 | 6/2007 | Cesarini et al. |
| 8,062,214 B2 | 11/2011 | Shener et al. |
| 9,060,760 B2 | 6/2015 | Sullivan et al. |
| 2001/0005778 A1* | 6/2001 | Ouchi ............... A61B 10/0275 606/171 |
| 2002/0045842 A1 | 4/2002 | Van Bladel et al. |
| 2005/0054948 A1* | 3/2005 | Goldenberg ......... A61B 10/025 600/567 |
| 2006/0116605 A1* | 6/2006 | Nakao ............... A61B 10/0266 600/566 |
| 2006/0155210 A1* | 7/2006 | Beckman ........... A61B 10/0275 600/564 |
| 2007/0213755 A1 | 9/2007 | Beckman et al. |
| 2008/0281223 A1* | 11/2008 | Goldenberg ....... A61B 10/0266 600/564 |
| 2009/0270812 A1 | 10/2009 | Litscher et al. |
| 2009/0270898 A1 | 10/2009 | Chin et al. |
| 2010/0152611 A1 | 6/2010 | Parihar et al. |
| 2010/0312140 A1 | 12/2010 | Smith et al. |
| 2013/0030322 A1 | 1/2013 | Levine |
| 2013/0046316 A1 | 2/2013 | Sullivan et al. |
| 2013/0211321 A1 | 8/2013 | Dubois et al. |
| 2015/0119795 A1 | 4/2015 | Germain |
| 2018/0360495 A1* | 12/2018 | Adams .................. A61B 10/04 |

* cited by examiner

TISSUE REMOVAL SYSTEM

RELATED APPLICATION DATA

The present application is a continuation of U.S. patent application Ser. No. 15/915,409, filed Mar. 8, 2018, now issued as U.S. Pat. No. 10,874,380, which is a continuation of U.S. patent application Ser. No. 15/556,599, filed Sep. 7, 2017, now issued as U.S. Pat. No. 9,913,629, which is a National Phase entry under 35 U.S.C § 371 of International Patent Application No. PCT/US2016/062080, having an international filing date of Nov. 15, 2016, which claims the benefit under 35 U.S.C. § 119 to U.S. provisional patent application Ser. No. 62/255,650, filed Nov. 16, 2015. The foregoing applications are hereby incorporated by reference into the present application in their entirety.

FIELD

The disclosure relates generally to methods, systems and devices for surgical procedures, and relates more particularly to tissue removal systems for the removal of body tissues, including uterine polyps and other abnormal gynecological tissues.

BACKGROUND

There are many situations in which it is desirable to remove unwanted tissue from a patient. Uterine polyps and uterine fibroids represent two such types of unwanted tissue. Uterine polyps are wispy masses that are commonly found extending from the inner lining of the uterus. Uterine fibroids are well-defined, non-cancerous tumors that are commonly found in the smooth muscle layer of the uterus. In many instances, uterine polyps and uterine fibroids can grow to be several centimeters in diameter and may cause symptoms like menorrhagia (prolonged or heavy menstrual bleeding), pelvic pressure or pain, and reproductive dysfunction. It is believed that uterine polyps occur in up to 10 percent of all women, and that uterine fibroids occur in a substantial percentage of the female population, perhaps in at least 20 to 40 percent of all women.

One type of treatment for uterine polyps and uterine fibroids is hysteroscopic resection. Hysteroscopic resection typically involves inserting a hysteroscope (i.e., an imaging scope) into the uterus through the vagina, i.e., transcervically, and then cutting away the unwanted tissue from the uterus using a device delivered to the unwanted tissue by or through the hysteroscope. Hysteroscopic resections typically fall into one of two varieties. In one variety, an electrocautery device in the form of a loop-shaped cutting wire is fixedly mounted on the distal end of the hysteroscope. The combination of the hysteroscope and the electrocautery device is typically referred to as a resectoscope. The transmission of electrical current to the uterus with a resectoscope is typically monopolar, and the circuit is completed by a conductive path to the power unit for the device through a conductive pad applied to the patient's skin. In this manner, tissue is removed by contacting the loop with the part of the uterus wall of interest. Examples of such devices are disclosed, for example, in U.S. Pat. No. 5,906,615, issued May 25, 1999, the contents of which are fully incorporated herein by reference as though set forth in full.

In the other variety of hysteroscopic resection, an electromechanical cutter is inserted through a working channel in the hysteroscope. The electromechanical cutter typically includes (i) a tubular member having a window through which tissue may enter and (ii) a cutting instrument positioned within the tubular member for cutting the tissue that has entered the tubular member through the window. In use, a distal portion of the electromechanical cutter is positioned near the part of the uterus wall of interest. Tissue is then drawn, typically by suction, into the window, and then the tissue drawn into the window is cut with the cutting instrument. Examples of the electromechanical cutter variety of hysteroscopic resection are disclosed in, for example, U.S. Pat. No. 9,060,760, issued Jun. 23, 2015; U.S. Pat. No. 8,062,214, issued Nov. 22, 2011; U.S. Pat. No. 7,226,459, issued Jun. 5, 2007; U.S. Pat. No. 6,032,673, issued Mar. 7, 2000; U.S. Pat. No. 5,730,752, issued Mar. 24, 1998; U.S. Patent Application Publication No. US 2009/0270898 A1, published Oct. 29, 2009; U.S. Patent Application Publication No. US 2009/0270812 A1, published Oct. 29, 2009; and PCT International Publication No. WO 99/11184, published Mar. 11, 1999, the contents of all of which are fully incorporated herein by reference as though set forth in full.

In both of the above-described varieties of hysteroscopic resection, prior to tissue removal, the uterus is typically distended to create a working space within the uterus. Such a working space typically does not exist naturally in the uterus because the uterus is a flaccid organ. As such, the walls of the uterus are typically in contact with one another when in a relaxed state. The conventional technique for creating such a working space within the uterus is to administer a fluid to the uterus through the hysteroscope under sufficient pressure to cause the uterus to become distended. Examples of the fluid used conventionally to distend the uterus include gases like carbon dioxide or, more commonly, liquids like water or certain aqueous solutions (e.g., a saline or other physiologic solution or a sugar-based or other non-physiologic solution). For instance, a 3 L bag of saline connected to a uterus (e.g., through a hysteroscope) can generate uterine distension pressure 50-60 mm of Hg.

One of the benefits of fluid distension is the tamponade effect that the distension fluid provides on resected vascular tissue. Since the distension fluid is typically maintained at a pressure that exceeds the patient's mean arterial pressure (MAP), the fluid pressure provided by the distension fluid prevents the leakage of arterial blood from the resected tissue from flowing or oozing into the uterine cavity. When arterial blood flows or oozes into the cavity, it mixes with the distension fluid and renders visualization more difficult and, if not constrained, the flowing or oozing blood will force the suspension of the procedure. Thus, maintenance of fluid pressure above the intracavity arterial pressure facilitates the maintenance of a clear visual field.

Nevertheless, one shortcoming with existing hysteroscopic tissue removal systems, particularly of the electromechanical cutter variety, is that it is often difficult to maintain fluid distension of the uterus during the resection procedure. This is because such systems typically employ a vacuum source that continuously subjects the electromechanical cutter to suction, even when the cutting mechanism of the electromechanical cutter is not switched on. The purpose of such suction is to draw tissue into the cutter, typically through the window, and to facilitate the removal of resected tissue from the uterus. However, such suction also typically has the unwanted effect of removing some of the distending fluid from the uterus along with the resected tissue. Moreover, because suction is continuously applied to the cutter, even when the cutting mechanism is not being operated, fluid tends to be continuously removed from the uterus whenever the cutter is inserted into the patient. If such fluid cannot be replenished quickly enough, the fluid pressure within the uterus may drop to an undesired level. In particular, a steep drop in uterine fluid pressure will result in the leakage of blood into the uterine cavity, causing a loss of visualization and ultimately stoppage of the procedure if the surgeon can no longer properly visualize the treatment site. Moreover, depending on the extent and speed of the drop in uterine fluid pressure, there may be a significant lapse of time before the uterine fluid pressure can be restored to a desired level such that adequate visualization is possible. Such lapses in time are clearly undesirable as they interrupt the resection procedure, as well as lengthen the overall time for the procedure and increase the risk that distending fluid may be taken up by a blood vessel in the uterus, i.e., intravasation, which uptake may be quite harmful to the patient.

One approach to the above problem has been to provide the electromechanical cutter with a mechanism actuated by an electrical switch that causes the window in the cutter to be closed off when the cutting mechanism is turned off. In this manner, when the cutting mechanism is switched off, only a minimal amount of distension fluid can escape from the uterus through the resection window of the cutter, and adequate uterine fluid pressure may be maintained. Unfortunately, the cost of the above-described electromechanical cutters may be prohibitive for certain procedures, such as polypectomies, for which the costs covered by most insurers are typically relatively low.

SUMMARY

In accordance with one embodiment, a tissue removal device for acquiring one or more samples of intrauterine tissue from a patient includes a housing. The device also includes an outer tube having a distal portion configured for transcervical insertion into a uterus, the outer tube having an outer tube lumen, a tissue in-take opening proximate a distal end thereof, and a proximal end coupled to the housing. The device further includes an inner tube slidably disposed within the outer tube lumen, the inner tube having an inner tube lumen extending from an open inner tube distal end to an open inner tube proximal end, the open inner tube distal end comprising a cutting edge configured to sever intrauterine tissue extending through the tissue in-take opening in the outer tube. Moreover, the device includes a vacuum generation chamber disposed within the housing. In addition, the device includes a movable piston slidably disposed in the vacuum generation chamber so that the piston forms a wall of the vacuum chamber. The inner tube lumen is selectively placed in fluid communication with the vacuum generation chamber via a distal one-way valve, the distal one-way valve being oriented so that material located in the inner tube lumen may be aspirated from the inner tube lumen into the vacuum generation chamber in response to movement of the piston in a distal direction, while material in the vacuum generation chamber is prevented by the distal one-way valve from entering the inner lumen. The device also includes a collection chamber. The vacuum generation chamber is selectively placed in fluid communication with the collection chamber via a proximal one-way valve, the proximal one-way valve being oriented so that material located in the vacuum generation chamber may be expelled from the vacuum generation chamber into the collection chamber in response to movement of the piston in a proximal direction, while material in the collection chamber is prevented from entering the vacuum generation chamber. The device further includes a manual actuator moveably coupled to the housing and operatively coupled to the piston, wherein movement of the actuator relative to the housing causes movement of the piston within the vacuum generation chamber.

In one or more embodiments, the in-take opening is a side facing opening relative to the outer tube. The distal one-way valve may be opened when the piston is moved in the distal direction and sealed when the piston is moved in the proximal direction. The proximal one-way valve may be opened when the piston is moved in the proximal direction and sealed when the piston is moved in the distal direction. The material may be intrauterine tissue or fluid from within the uterus. The proximal and distal one-way valves may be duck-billed valves.

In one or more embodiments, the device also includes a porous filter trap in selective fluid communication with the vacuum generation chamber, the porous filter trap configured to separate excised intrauterine tissue from fluid. The porous filter trap may be contained in the collection chamber. The porous filter trap may be selectively fluidly coupled to the vacuum generation chamber by the proximal one-way valve, so that material may pass from the vacuum generation chamber to the porous filter trap in response to movement of the piston in a proximal direction. The porous filter trap may be integrally formed. The device may also include a trap housing configured to releasably secure the porous filter trap onto the housing. The outer tube may include an edge adjacent the tissue in-take opening configured to facilitate collection of intrauterine tissue adjacent the tissue in-take opening. When the actuator is fully actuated, a volume of the vacuum generation chamber may be about three times a volume of the inner tube lumen.

In one or more embodiments, the proximal and distal one-way valves are configured such that, when the piston is not moving and the uterus is distended by distension fluid, both the proximal and distal one-way valves are open under pressure from the distension fluid. The proximal and distal one-way valves may be configured such that, when the piston is not moving and the uterus is distended by distension fluid, the distension fluid flows through the proximal and distal one-way valves. The distension fluid may urge intrauterine tissue through the tissue in-take opening and into an outer tube lumen. The proximal and distal one-way valves may each have a cracking pressure of about 40 mm Hg and the distension fluid may generate a distension pressure between about 50 mm Hg and about 60 mm Hg. The distal one-way valve may be at least partially formed in the piston.

In one or more embodiments, the device also includes a valve configured to selectively couple the inner tube lumen with a vacuum source external to the housing. The valve may be a pinch valve.

In one or more embodiments, the manual actuator may be operatively coupled to the inner tube such that movement of the actuator relative to the housing causes longitudinal movement of the inner tube within the outer tube lumen. The device may also include a cam and a cam follower operatively coupled to the inner tube and the housing such that movement of the actuator relative to the housing causes longitudinal and rotational movement of the inner tube within the outer tube lumen. The cam may be fixed to the inner tube and the cam follower may be fixed to the housing. The cam may be fixed to the housing and the cam follower may be fixed to the inner tube.

In one or more embodiments, the device also includes a yoke selectively coupling the manual actuator to the inner tube. When the manual actuator is coupled to the inner tube, movement of the actuator relative to the housing causes longitudinal movement of the piston within the vacuum generation chamber and the inner tube within the outer tube lumen. When the manual actuator is uncoupled from the inner tube, longitudinal movement of the actuator relative to the housing causes the piston within the vacuum generation chamber without longitudinal movement of the inner tube within the outer tube lumen. The device may include a knob configured to rotate the outer tube relative to the housing to change a circumferential position of the opening.

In accordance with one embodiment, a tissue removal device for acquiring one or more samples of intrauterine tissue from a patient includes a housing. The device also includes an outer tube having a distal portion configured for transcervical insertion into a uterus, the outer tube having an outer tube lumen, a tissue in-take opening proximate a distal end thereof, and a proximal end coupled to the housing. The device further includes an inner tube slidably disposed within the outer tube lumen, the inner tube having an inner tube lumen extending from an open inner tube distal end to an open inner tube proximal end, the open inner tube distal end comprising a cutting edge configured to sever intrauterine tissue extending through the tissue in-take opening in the outer tube. Moreover, the device includes a vacuum generation chamber disposed within the housing. In addition, the device includes a bellows disposed within the housing and having a movable wall and a vacuum generation chamber. The inner tube lumen is selectively placed in fluid communication with the vacuum generation chamber via a distal one-way valve, the distal one-way valve being oriented so that material located in the inner tube lumen may be aspirated from the inner tube lumen into the vacuum generation chamber in response to movement of the wall of the bellows in a distal direction, while material in the vacuum generation chamber is prevented by the distal one-way valve from entering the inner lumen. The device also includes a collection chamber. The vacuum generation chamber is selectively placed in fluid communication with the collection chamber via a proximal one-way valve, the proximal one-way valve being oriented so that material located in the vacuum generation chamber may be expelled from the vacuum generation chamber into the collection chamber in response to movement of the wall of the bellows in a proximal direction, while material in the collection chamber is prevented from entering the vacuum generation chamber. The device further includes a manual actuator moveably coupled to the housing and operatively coupled to the wall of the bellows, wherein movement of the actuator relative to the housing causes movement of the wall of the bellows within the vacuum generation chamber. In one or more embodiments, the wall of the bellows is a distal wall.

Additional objects, as well as aspects, features and advantages, of the disclosure are set forth in part in the description which follows, and in part will be obvious from the description or may be learned by practice of the invention. In the description, reference is made to the accompanying drawings which form a part thereof and in which is shown by way of illustration various embodiments for practicing the invention. The embodiments will be described in sufficient detail to enable those skilled in the art to practice the invention, and it is to be understood that other embodiments may be utilized and that structural changes may be made without departing from the scope of the disclosed inventions. The following detailed description is, therefore, not to be taken in a limiting sense, and the scope of the disclosure is best defined by the appended claims.

BRIEF DESCRIPTION OF THE DRAWINGS

The drawings illustrate the design and utility of embodiments of the disclosed inventions, in which similar elements are referred to by common reference numerals. These drawings are not necessarily drawn to scale. In order to better appreciate how the above-recited and other advantages and objects are obtained, a more particular description of the embodiments will be rendered, which are illustrated in the accompanying drawings. These drawings depict only typical embodiments of the disclosed inventions and are not therefore to be considered limiting of its scope.

DETAILED DESCRIPTION

Figure 1:
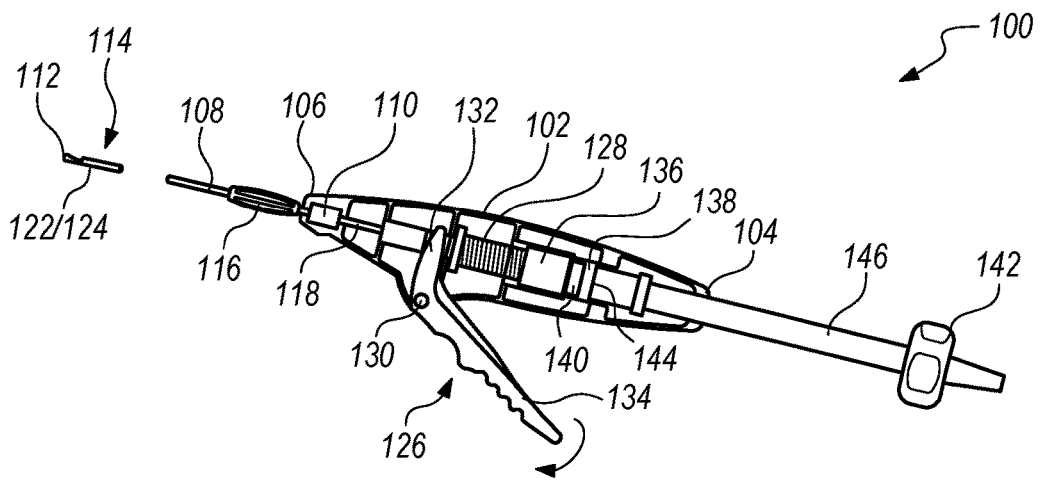
FIG. 1 is a side view of a first embodiment of a tissue removal device constructed according to the teachings of the disclosure, with an actuator of the tissue removal device in an un-actuated state, and with a portion of a housing removed.

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skilled in the art would consider equivalent to the recited value (i.e., having the same function or result). In many instances, the terms "about" may include numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

As used in this application, a "tubular member" is any elongate device having a lumen. The lumen may extend the entire length of the elongate device (i.e., from a first end to a second, opposite end), or the lumen may extend less than the entire length of the elongate device. A tubular member can be formed from any material, including, but not limited to, metals and polymers. While the tubular members described herein have substantially circular cross-sectional geometry, tubular members may have any cross-sectional geometry, including one that changes along the longitudinal axis of the device. Therefore, uses of terms that connote circular geometry, such as "radius," "diameter," "circumference," and "annular," are illustrative, and not intended to be limiting. Accordingly, such terms are intended to include analogous concepts in tubular members having non-circular geometries.

Conditional language, such as, among others, "can," "could," "might," or "may," unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment. The headings used herein are for the convenience of the reader only and are not meant to limit the scope of the inventions or claims.

Various embodiments are described hereinafter with reference to the figures. The figures are not necessarily drawn to scale, the relative scale of select elements may have been exaggerated for clarity, and elements of similar structures or functions are represented by like reference numerals throughout the figures. It should also be understood that the figures are only intended to facilitate the description of the embodiments, and are not intended as an exhaustive description of the invention or as a limitation on the scope of the invention, which is defined only by the appended claims and their equivalents. In addition, an illustrated embodiment needs not have all the aspects or advantages shown. An aspect or an advantage described in conjunction with a particular embodiment is not necessarily limited to that embodiment and can be practiced in any other embodiments even if not so illustrated.

The disclosure is described below primarily in the context of devices and procedures optimized for performing one or more therapeutic or diagnostic gynecological or urological procedures such as the removal of uterine polyps or other uterine tissue. However, the devices and related procedures of the disclosure may be used in a wide variety of applications throughout the body, through a variety of access pathways.

For example, the devices of the disclosure can be optimized for use via open surgery, less invasive access such as laparoscopic access, or minimally invasive procedures such as via percutaneous access. In addition, the devices of the disclosure can be configured for access to a therapeutic or diagnostic site via any of the body's natural openings to accomplish access via the ears, nose, mouth, and via transrectal, urethral and vaginal approach.

In addition to the performance of one or more gynecological and urologic procedures described in detail herein, the systems, methods, apparatus and devices of the disclosure may be used to perform one or more additional procedures, including, but not limited to, access to and tissue manipulation or removal from any of a variety of organs such as the bladder, breast, lung, stomach, bowel, esophagus, oral cavity, rectum, nasal sinus, Eustachian tubes, heart, gall bladder, arteries, veins, and various ducts. Routes of access include but are not limited to trans-cervical; trans-vaginal-wall; trans-uteral; trans-vesicle; trans-urethral; and other routes.

FIGS. 1-4 illustrate an embodiment of a tissue removal device 100 in respective un-actuated (FIGS. 1 and 3) and actuated (FIGS. 2 and 4) states (described below). The tissue removal device 100 includes manually operated assemblies (also described below) for creating vacuum and for cutting tissue. As used in this application, "vacuum" includes but is not limited to, a pressure differential sufficient to move material (e.g., excised tissue and fluid) from one space to another space. As such, the tissue removal device 100 is capable of performing a tissue removal procedure (e.g., a polypectomy) with no external vacuum or power sources, and is therefore a "tetherless" or "non-tethered" device. This is in contrast to "tethered" tissue removal devices, which require various external power sources, motors, and/or vacuums to perform tissue removal procedures.

Figure 3:
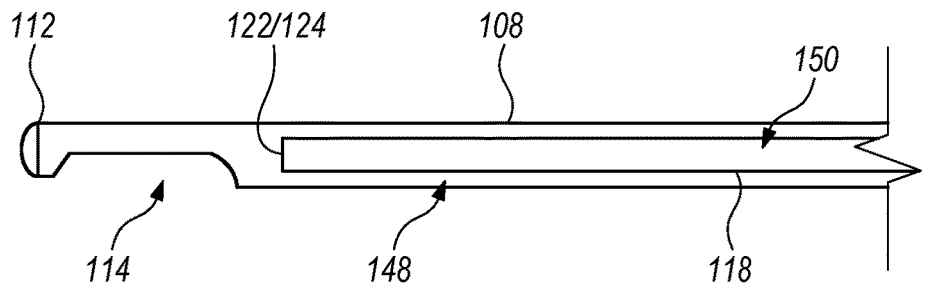
FIG. 3 is a detailed cross-sectional side view of respective distal ends of outer and inner tubular members of the tissue removal device depicted in FIG. 1, with the actuator of the tissue removal device in an un-actuated state.
Figure 4:
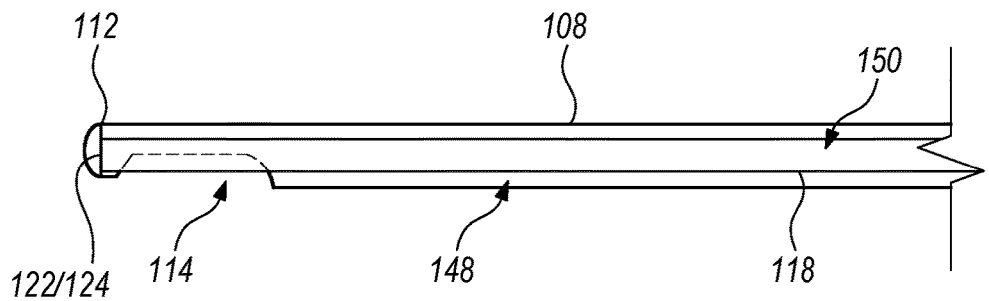
FIG. 4 is a detailed cross-sectional side view of respective distal ends of outer and inner tubular members of the tissue removal device depicted in FIG. 1, with the actuator of the tissue removal device in an actuated state.

The tissue removal device 100 includes a housing 102 having a proximal end 104 and a distal end 106. The tissue removal device 100 also includes an outer tubular member 108 having a proximal end 110 rotatably coupled to the distal end 106 of the housing 102 and a distal end 112 having a proximal tissue receiving window/tissue in-take opening 114, as best shown in FIGS. 3 and 4. The outer tubular member 108 also includes a grip/rotator/knob 116 configured to facilitate user rotation of the rotatably coupled outer tubular member 108. The rotator 116 is disposed adjacent and fixed to the proximal end 110 of the outer tubular member 108. In this manner, the outer tubular member 108 is configured to selectively rotate relative to the housing 102 in response to manipulation of the rotator 116 to alter the circumferential position of the tissue receiving window 114. The tissue removal device 100 further includes an inner tubular member 118 configured for axial movement within an outer tubular member lumen 148 in the outer tubular member 108, as shown in FIGS. 3 and 4. The outer and inner tubular members 108, 118 can be either flexible or rigid.

The outer tubular member 108 may be configured for transcervical insertion. Additionally or alternatively, the outer tubular member 108 may be configured for insertion through a working channel of an endoscopic instrument so that the tissue receiving window 114 is disposed in an interior region of a patient's body. The distal end 112 of the outer tubular member 108 may be conformable or rigid. The inner tubular member 118 is hollow, and includes an open proximal end, an open distal end 122, and an inner tubular member lumen 150 (see FIGS. 3 and 4) extending between the open proximal end 120 and the open distal end 122. The distal end 122 of the inner tubular member 118 includes a cutting edge 124 (e.g., annular) for severing tissue projecting into the tissue receiving window 114 as the inner tubular member 118 moves past the tissue receiving window 114 (see FIGS. 3 and 4).

The tissue removal device 100 also includes a manually operated actuator, or trigger 126 rotatably coupled to the housing 102 by a pinned connection 130, which acts as a pivot point, such that the trigger 126 is configured to rotate about the pinned connection 130. The trigger 126 includes a first end 132 disposed inside of the housing 102, and a second end 134 disposed outside of the housing 102. The trigger 126 is rotatably coupled to the housing 102 such that a user may hold the housing 102 in one hand and actuate the trigger 126 by squeezing the second end 134 of the trigger 126 toward the housing 102. Actuating the trigger 126 by squeezing rotates the second end 134 of the trigger 126 toward the housing 102 about the pivot point formed by the pinned connection 130. A spring 128 is configured to bias the second end 134 of the trigger 126 away from the housing 102, as shown in FIG. 1. As a result, when the trigger 126 is released after being actuated, the spring 128 restores the second end 134 of the trigger 126 to its un-actuated position away from the housing 102. The spring 128 may be coupled to the housing 102 and the first end 132 of the trigger 126. It should be understood that the individual components of the device 100 illustrated in FIGS. 1-4 are not necessarily drawn to scale. Further, FIGS. 1-4 are provided to illustrate the principles of the disclosed embodiments, and are not intended to be limiting.

Figure 2:
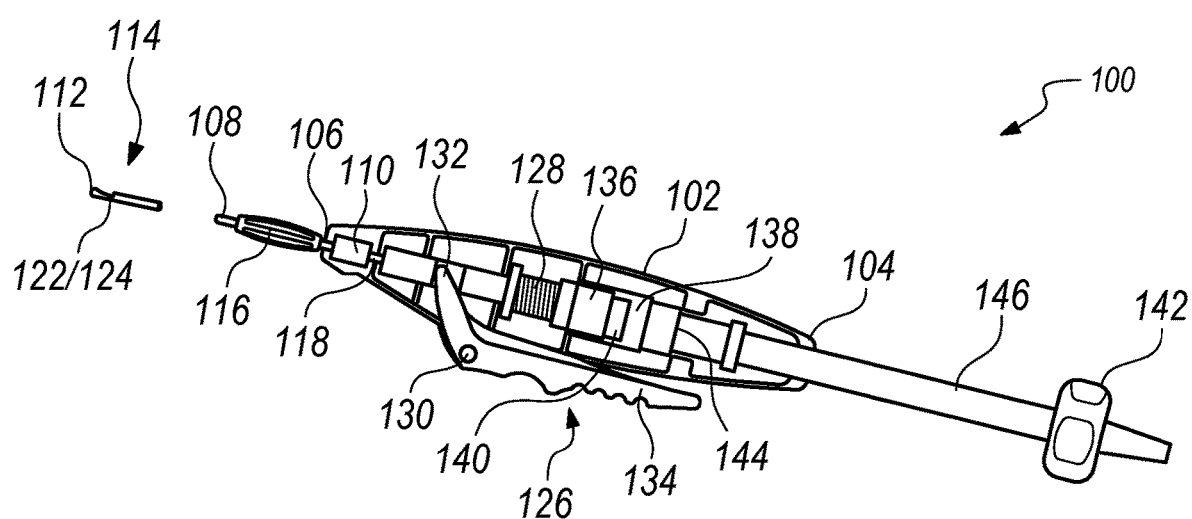
FIG. 2 is a side view of the tissue removal device depicted in FIG. 1, with the actuator of the tissue removal device in an actuated state, and with a portion of the housing removed.

The first end 132 of the trigger 126 is coupled to a piston/plunger 136, which forms a movable distal wall of a vacuum generation chamber 138, thereby enabling the vacuum generation chamber 138 to change its volume with movement of the piston/plunger 136. Actuating the trigger 126 rotates the first end 132 of the trigger 126 about the pinned connection 130, and moves the piston 136 relative to a proximal wall of the vacuum generation chamber 138. In particular, actuating the second end 134 of the trigger 126 toward the housing 102 causes the piston 136 to be pulled distally away from the proximal wall of the vacuum generation chamber 138, thereby increasing the volume of the vacuum generation chamber 138 and reducing the pressure therein to generate vacuum, as shown in FIG. 2. In one embodiment, when the trigger 126 is fully actuated (i.e., moved maximally toward the housing 102), a volume of the vacuum generation chamber 138 is increased to about three times a volume of the inner tubular member lumen 150. In some embodiments, this volume ratio optimizes vacuum generation and tissue travel through the inner tubular member lumen 150, and minimizes tissue clogging therein.

Releasing the trigger 126 allows the spring 128 to restore the second end 134 of the trigger 126 to its un-actuated position away from the housing 102. When the trigger 126 is restored to its un-actuated position, the piston 136 is pushed proximally toward the proximal wall of the vacuum generation chamber 138, thereby decreasing the volume of the vacuum generation chamber 138 and increasing the pressure therein, as shown in FIG. 1.

The proximal end 120 of the inner tubular member 118 may be fluidly coupled to and/or form part of the piston/plunger 136. The vacuum generation chamber 138 is selectively fluidly coupled to the proximal end 120 of the inner tubular member 118 through a distal one-way valve 140 (e.g., a duck-bill valve). The distal one-way valve 140 may be fluidly coupled to and/or form a part of a proximal end of the piston/plunger 136. The distal one-way valve 140 is configured to open when vacuum is generated in the vacuum generation chamber 138, thereby allowing severed tissue and/or fluid to be drawn from the inner tubular member lumen 150 into the vacuum generation chamber 138. The distal one-way valve 140 is also configured to close when pressure is increased in the vacuum generation chamber 138, thereby preventing severed tissue and/or fluid from being pushed from the vacuum generation chamber 138 into the inner tubular member lumen 150.

In particular, the distal one-way valve 140 is configured to open when the pressure distal of the distal one-way valve 140 (i.e., in the inner tubular member lumen 150) (the "distal pressure") is approximately 20 mm Hg to 120 mm Hg greater than the pressure proximal of the distal one-way valve 140 (i.e., in the vacuum generation chamber 138) (the "proximal pressure"). Preferably, the distal one-way valve 140 is configured to open when the distal pressure is approximately 50 mm Hg greater than the proximal pressure. The distal one-way valve 140 is also configured to remain at least partially open as long as the distal pressure is at least approximately 50 mm Hg greater than the proximal pressure. When the distal pressure is less than approximately 50 mm Hg greater than the proximal pressure (or the proximal pressure is greater than the distal pressure), the distal one-way valve 140 will be closed.

The vacuum generation chamber 138 is also selectively fluidly coupled to a specimen collection chamber 142 through a proximal one-way valve 144 (e.g., a duck-bill valve). The proximal one-way valve 144 may be fluidly coupled to or form a part of a distal end of a connector 146 fluidly coupling the vacuum generation chamber 138 to the specimen collection chamber 142. The proximal one-way valve 144 is configured to open when a pressure in the vacuum generation chamber 138 is greater than a pressure in the specimen collection chamber 142 (i.e., the reverse of the distal one-way valve 140), thereby allowing severed tissue and/or fluid to be pushed from the vacuum generation chamber 138 into the specimen collection chamber 142. The proximal one-way valve 144 is also configured to close when vacuum is generated in the vacuum generation chamber 138 (i.e., the reverse of the distal one-way valve 140), thereby preventing severed tissue and/or fluid (e.g., air) from being drawn from proximal portions of the device 100 (e.g., the specimen collection chamber 142 or the connector 146) into the vacuum generation chamber 138.

In particular, the proximal one-way valve 144 is configured to open when the pressure distal of the proximal one-way valve 144 (i.e., in the vacuum generation chamber 138) (the "distal pressure") is approximately 20 mm Hg to 120 mm Hg greater than the pressure proximal of the proximal one-way valve 144 (i.e., in the connector 146 and the specimen collection chamber 142) (the "proximal pressure"). Preferably, the proximal one-way valve 144 is configured to open when the distal pressure is approximately 50 mm Hg greater than the proximal pressure. The proximal one-way valve 144 is also configured to remain at least partially open as long as the distal pressure is at least approximately 50 mm Hg greater than the proximal pressure. When the distal pressure is less than approximately 50 mm Hg greater than the proximal pressure (or the proximal pressure is greater than the distal pressure), the proximal one-way valve 144 will be closed.

While in this embodiment, the pressure differentials are achieved by changing the pressure in the vacuum generation chamber 138, the pressure differentials can also be achieved by changing the pressure in the inner tubular member lumen 150 (for the distal one-way valve 140), and the connector 146 and the specimen collection chamber 142 (for the proximal one-way valve 144). In embodiments where the distal and proximal one-way valves 140, 144 are duck-billed valves, the "bills" are facing proximally to allow severed tissue and fluid to travel from the inner tubular member lumen 150 into the vacuum generation chamber 138, and then into the connector 146 and the specimen collection chamber 142. This valve configuration also minimizes backflow of allow severed tissue and fluid from the specimen collection chamber 142 and the connector 146 into the vacuum generation chamber 138, and then into the inner tubular member lumen 150.

The proximal end 120 of the inner tubular member 118 is either physically coupled to or forms part of the piston/plunger 136. Accordingly, actuating the trigger 126 also moves the inner tubular member 118 longitudinally/axially within the outer tubular member 108. The distance covered by the inner tubular member 118 during actuating the trigger 126 is greater than the length of the tissue receiving window 114 in the outer tubular member 108. Actuating the trigger 126 rotates the trigger 126 about the pinned connection 130, and moves the inner tubular member 118 relative to the outer tubular member 108. In particular, actuating the second end 134 of the trigger 126 toward the housing 102 causes the inner tubular member 118 to be pushed distally within the outer tubular member 108, as shown in FIGS. 2 and 4. Distal movement of the inner tubular member 118 within the outer tubular member 108 moves the cutting edge 124 at the distal end 122 of the inner tubular member 118 across the tissue receiving window 114, thereby severing any tissue prolapsing through the tissue receiving window 114, as shown in FIG. 4 (without the tissue). The tissue removal device 100 is configured such that the vacuum generated in the vacuum generation chamber 138 by actuating the trigger 126 draws tissue into the tissue receiving window 114 before the cutting edge 124 severs the tissue. The device 100 is also configured such that the vacuum generated in the vacuum generation chamber 138 by actuating the trigger 126 also draws severed tissue from the inner tubular member lumen 150 into the vacuum generation chamber 138 through the open distal one-way valve 140 (when there is low pressure in the vacuum generation chamber 138). The device 100 is further configured such that sufficient vacuum to pull tissue into the tissue receiving window and to pull severed tissue into the vacuum generation chamber 138 is created within the vacuum generation chamber 138 with a single squeeze of the trigger 126.

Releasing the trigger 126 allows the spring 128 to restore the trigger 126 to its un-actuated position with the second end 134 away from the housing 102. When the trigger 126 is restored to its un-actuated position, the inner tubular member 118 is pulled proximally within the outer tubular member 108, as shown in FIGS. 1 and 3. Proximal movement of the inner tubular member 118 within the outer tubular member 108 opens the tissue receiving opening as shown in FIG. 3. The tissue removal device 100 is configured such that the pressure generated in the vacuum generation chamber 138 by (e.g., the spring 128) restoring the trigger 126 to its un-actuated position pushes severed tissue from the vacuum generation chamber 138 into the specimen collection chamber 142 before the proximally traveling piston/plunger 136 reduces volume of the vacuum generation chamber 138 to less than the volume of the severed tissue. The device 100 is also configured such that sufficient pressure to push severed tissue into the specimen collection chamber 142 is created within the vacuum generation chamber 138 with a single restoration of the trigger 126 (e.g., by the spring 128).

As described above, each time the trigger 126 is actuated/squeezed, vacuum is created by the distally moving piston 136 in the vacuum generation chamber 138 and immediately applied to the tissue through the inner tubular member 118, pulling the tissue into the tissue receiving window 114 (see FIG. 4). Further, each time the trigger 126 is actuated/squeezed, the cutting edge 124 travels distally over the tissue receiving window 114, severing tissue prolapsing therethrough. Moreover, the vacuum generated by each trigger 126 actuation/squeeze also opens the distal one-way valve 140 and draws severed tissue (either from the current or a previous stroke) from the inner tubular member lumen 150 into the vacuum generation chamber 138.

Similarly, each time the spring 128 restores the trigger 126 to its un-actuated position, pressure is created by the proximally moving piston 136 in the vacuum generation chamber 138. The pressure in the vacuum generation chamber 138 closes the distal one-way valve 140 and opens the proximal one-way valve 144 due to the respective pressure differentials as described above. The pressure in the vacuum generation chamber 138 also pushes the severed tissue (if any) and fluid therein through the open proximal one-way valve 144, through the connector 146 and into the specimen collection chamber 142. As a result, any tissue or fluid (including air) drawn into the device 100 by the vacuum during trigger 126 actuation is off-set by an equal volume of tissue and/or fluid that is ejected into the specimen collection chamber 142 (which may have a pressure vent during trigger 126 restoration, thereby preventing build-up of pressure in the device 100.)

Further, each time the trigger 126 is restored, the cutting edge 124 travels proximally across the tissue receiving window 114, opening the tissue receiving window 114 by moving the inner tubular member 118 previously blocking the window 114 proximally away from the window 114 (see FIG. 3). As such, repeatedly actuating the trigger 126 of the tissue removal device 100 efficiently severs tissue, and moves the severed tissue, using vacuum and pressure from the vacuum generation chamber 138, through the device 100 and into the specimen collection chamber 142. At the completion of a tissue removal procedure, the specimen collection chamber 142 with the severed tissue therein, can be removed from the device 100. In other embodiments, each time the trigger 126 is actuated/squeezed, the inner tubular member 118 and its cutting edge 124 are also rotated to facilitate tissue cutting along with the axial reciprocation. For instance, the tissue removal device can include a cam and cam follower (neither shown in FIGS. 1-4) or other components to transfer the actuation motion to rotation of the cutting edge 124 of the inner tubular member 118. An embodiment with a rotating inner tubular member is described below in FIGS. 17-19 and described below.

FIGS. 5-14 illustrate another embodiment of a tissue removal device 100' in respective un-actuated (FIGS. 8 and 10-12 and actuated (FIG. 9) states. The tissue removal device 100' includes manually operated assemblies for creating vacuum and for cutting tissue (described below). These vacuum generation and tissue cutting assemblies of the tissue removal device 100' are structurally and operationally similar to the vacuum generation and tissue cutting assemblies of the tissue removal device 100 depicted in FIGS. 1-4 and described above. Like the tissue removal device 100 depicted in FIGS. 1-4, the tissue removal device 100' depicted in FIGS. 5-12 is capable of performing a tissue removal procedure (e.g., a polypectomy) with no further components, and is therefore also a "tetherless" device.

Figure 5:
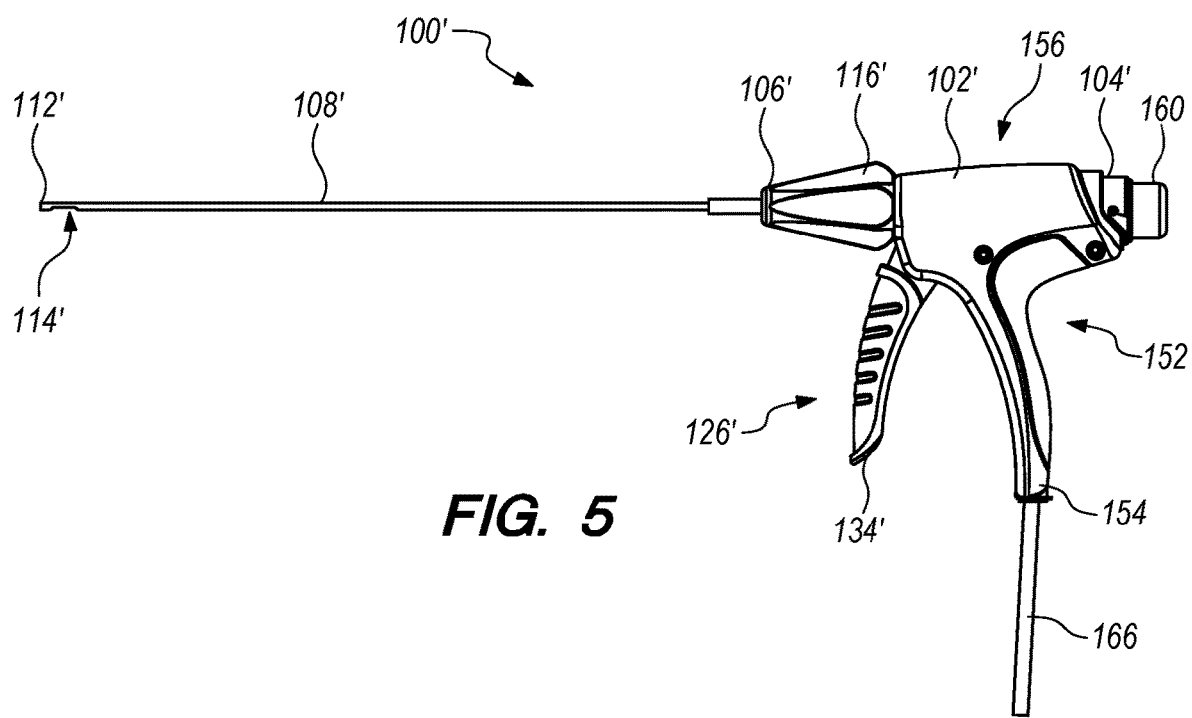
FIG. 5 is a side view of a second embodiment of a tissue removal device constructed according to the teachings of the disclosure, with an actuator of the tissue removal device in an un-actuated state.
Figure 6:
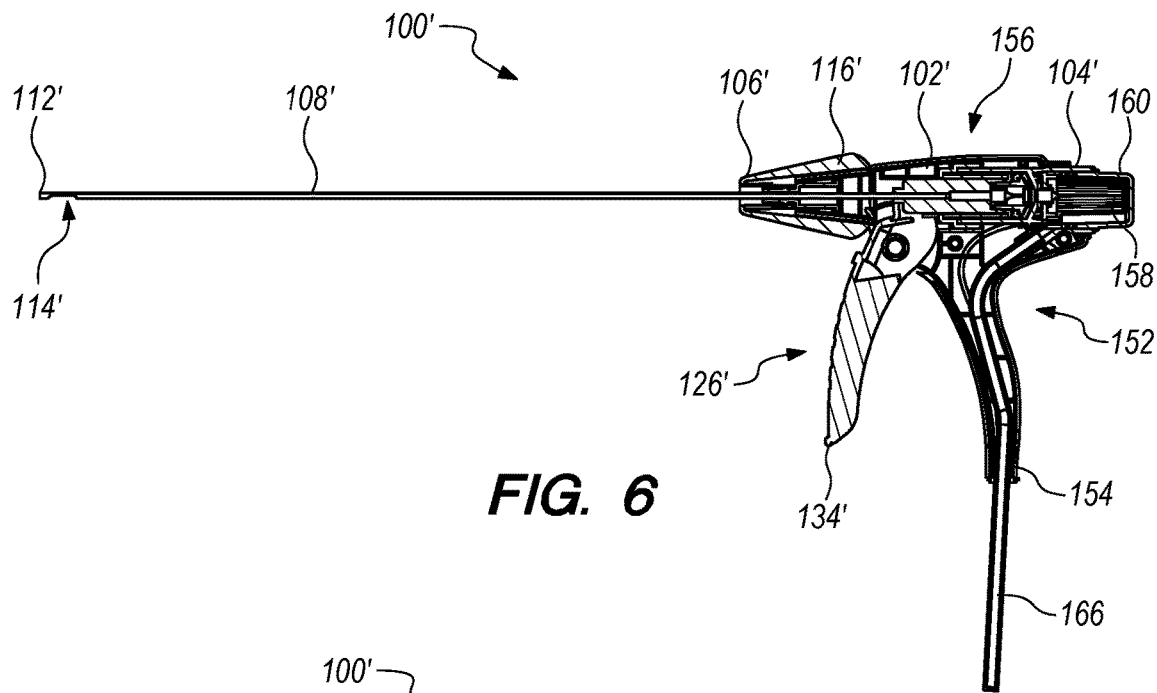
FIGS. 6-8 are increasingly detailed cross-sectional side views of the tissue removal device depicted in FIG. 5, with the actuator of the tissue removal device in an un-actuated state.
Figure 7:
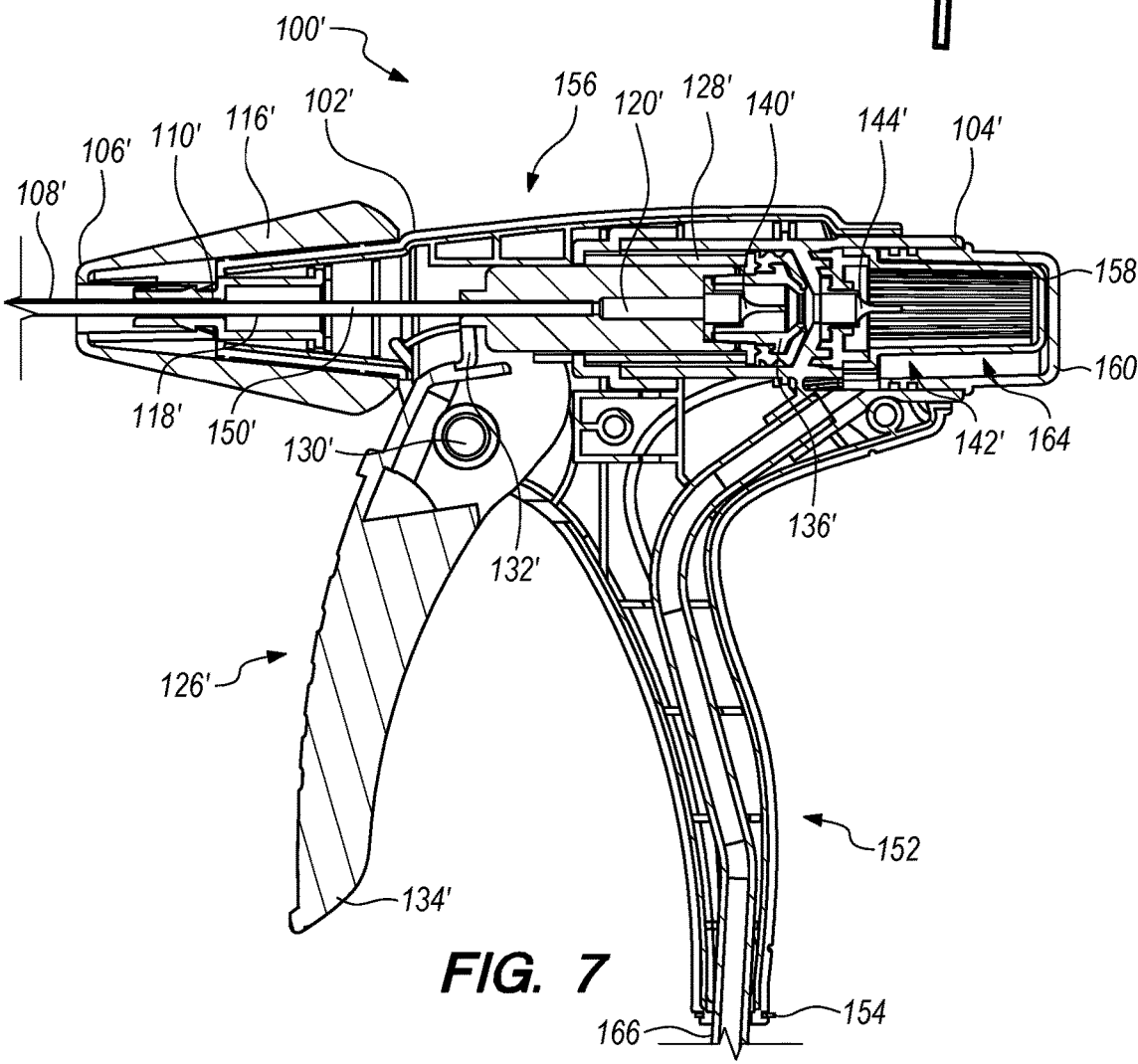
Figure 8:
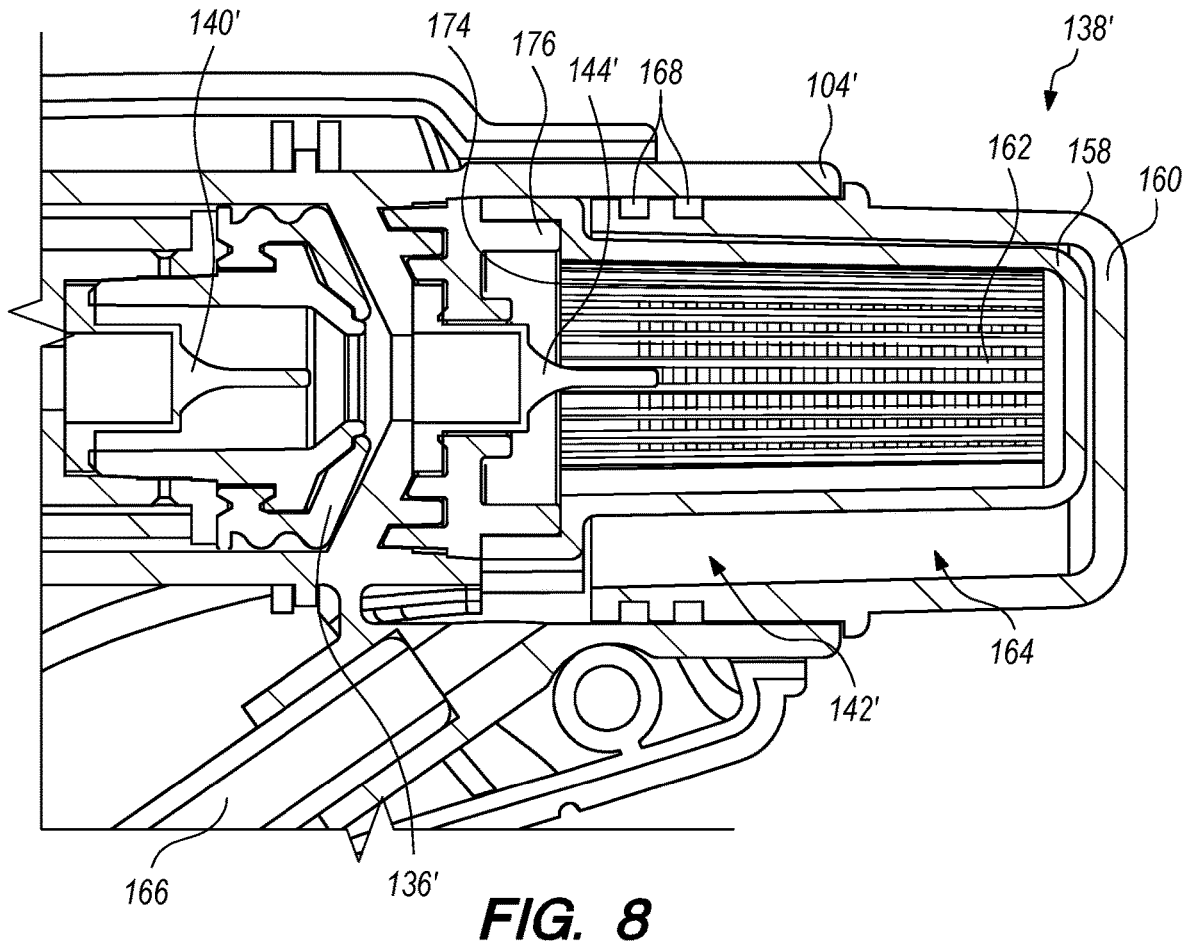

FIG. 5 depicts the tissue removal device 100' in an external side view. The tissue removal device 100' includes a pistol-shaped housing 102'. The more pistol-like shape of the tissue removal device 100' results in the tissue removal device 100' having a handle 152 with a bottom end 154 in addition to a body 156 with a distal end 106' and a proximal end 104'. The ergonomics of the pistol-shaped housing 102' also allows a user's hand to generate more power when actuating the tissue removal device 100'. FIGS. 6-8 are increasingly detailed cross-section views of the tissue removal device 100' depicted in FIG. 5, with FIG. 8 showing the specimen collection chamber 142' formed at the proximal end 104' of the housing 102' in detail.

Figure 13:
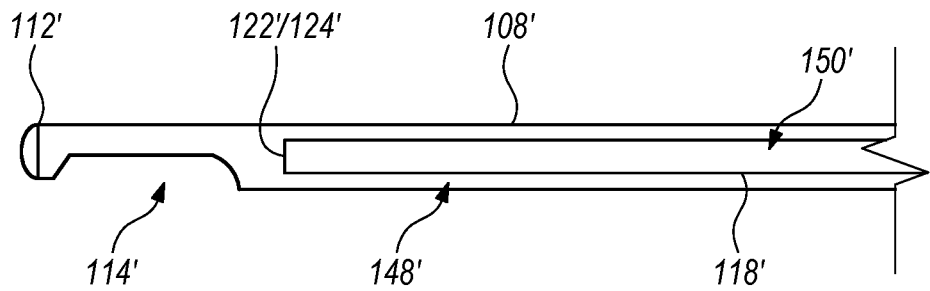
FIG. 13 is a detailed cross-sectional side view of respective distal ends of outer and inner tubular members of the tissue removal device depicted in FIG. 5, with the actuator of the tissue removal device in an un-actuated state.
Figure 14:
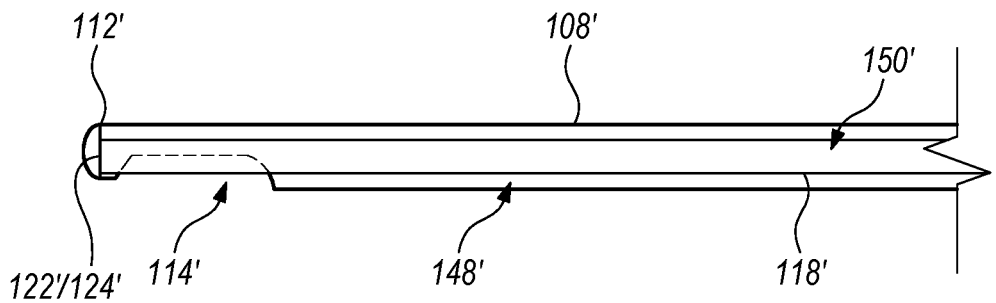
FIG. 14 is a detailed cross-sectional side view of respective distal ends of outer and inner tubular members of the tissue removal device depicted in FIG. 5, with the actuator of the tissue removal device in an actuated state.

The tissue removal device 100' also includes an outer tubular member 108' having a proximal end 110' (FIG. 7) rotatably coupled to the distal end 106' of the housing 102' and a distal end 112' having a tissue receiving window 114' (FIGS. 5 and 6). The outer tubular member 108' also includes a rotator 116' configured to facilitate user rotation of the rotatably coupled outer tubular member 108'. The rotator 116' is disposed adjacent and fixed to the proximal end 110' of the outer tubular member 108'. In this manner, the outer tubular member 108' is configured to selectively rotate relative to the housing 102' in response to manipulation of the rotator 116' to alter the circumferential position of the tissue receiving window 114'. In other embodiments, the rotator can be located at a proximal end of the tissue removal device. In such embodiments, the rotation may be coupled to the outer tubular member via a series of connectors and gears. The tissue removal device 100' further includes an inner tubular member 118' configured for axial movement within an outer tubular member lumen 148' in the outer tubular member 108', as shown in FIGS. 13 and 14. The outer and inner tubular members 108', 118' can be either flexible or rigid.

The outer tubular member 108' may be configured for transcervical insertion. Additionally or alternatively, the outer tubular member 108' may be configured for insertion through a working channel of an endoscopic instrument so that the tissue receiving window 114' is disposed in an interior region of a patient's body. The distal end 112' of the outer tubular member 108' may be conformable or rigid. The inner tubular member 118' is hollow, and includes an open proximal end 120' (see FIGS. 7 and 9), an open distal end 122', and an inner tubular member lumen 150' (see FIGS. 13 and 14) extending between the open proximal end 120' and the open distal end 122'. The distal end 122' of the inner tubular member 118' includes a cutting edge 124' (e.g., annular) for severing tissue projecting into the tissue receiving window 114' as the inner tubular member 118' moves past the tissue receiving window 114' (see FIGS. 13 and 14).

The tissue removal device 100' also includes a manually operated actuator, or trigger 126' rotatably coupled to the housing 102' by a pinned connection 130', which acts as a pivot point, such that the trigger 126' is configured to rotate about the pinned connection 130'. The trigger 126' includes a first end 132' disposed inside of the housing 102' in the body 156, and a second end 134' disposed outside of the housing 102'. In an un-actuated state, most of the trigger 126' is separated from and approximately parallel to the handle 152. The trigger 126' is rotatably coupled to the housing 102' such that a user may hold the housing 102' in one hand and actuate the trigger 126' by squeezing the second end 134' of the trigger 126' toward the handle 152. Actuating the trigger 126' by squeezing rotates the second end 134' of the trigger 126' toward the handle 152 about the pivot point formed by the pinned connection 130'. A spring 128' [not shown?] is configured to bias the second end 134' of the trigger 126' away from the handle 152, as shown in FIGS. 5-7. As a result, when the trigger 126' is released after being actuated, the spring 128' restores the second end 134' of the trigger 126' to its un-actuated position away from the handle 152. The spring 128' may be coupled to the housing 102' and the first end 132' of the trigger 126'. It should be understood that the individual components of the device 100' illustrated in FIGS. 5-14 are not necessarily drawn to scale. Further, FIGS. 5-14 are provided to illustrate the principles of the disclosed embodiments, and are not intended to be limiting.

Figure 9:
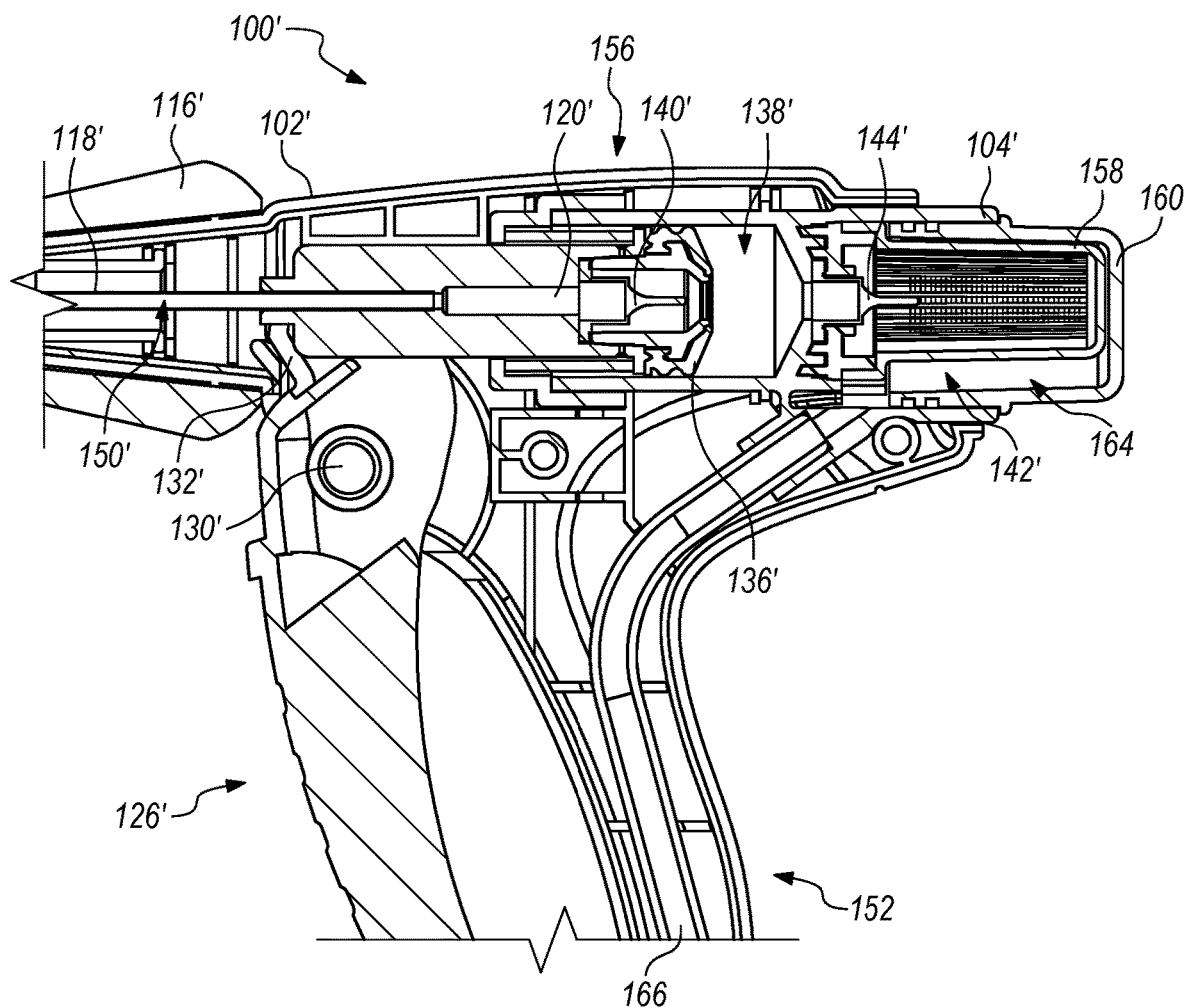
FIG. 9 is a detailed cross-sectional side view of the tissue removal device depicted in FIG. 5, with the actuator of the tissue removal device in an actuated state.
Figure 10:
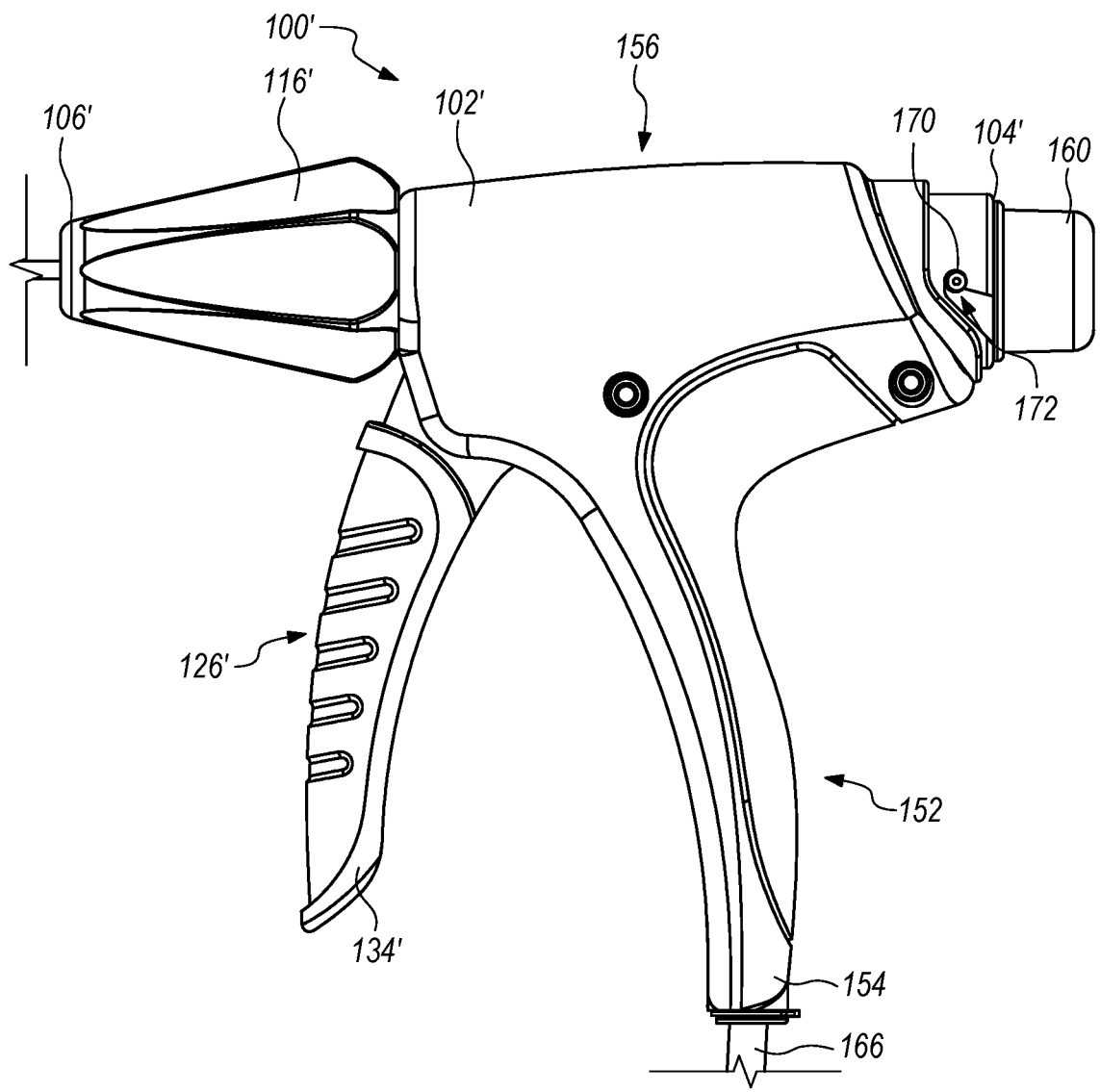
FIG. 10 is a side view of the tissue removal device depicted in FIG. 5, with the actuator of the tissue removal device in an un-actuated state.

The first end 132' of the trigger 126' is coupled to a piston/plunger 136', which forms a movable distal wall of the vacuum generation chamber 138', thereby enabling the vacuum generation chamber 138' to change its volume with movement of the piston/plunger 136'. Actuating the trigger 126' rotates the first end 132' of the trigger 126' about the pinned connection 130', and moves the piston 136' relative to a proximal wall of the vacuum generation chamber 138'. In particular, actuating the second end 134' of the trigger 126' toward the handle 152 causes the piston 136' to be pulled distally away from the proximal wall of the vacuum generation chamber 138', thereby increasing the volume of the vacuum generation chamber 138' and reducing the pressure therein to generate vacuum, as shown in FIG. 9. In one embodiment, when the trigger 126' is fully actuated (i.e., moved maximally toward the housing 102'), a volume of the vacuum generation chamber 138' is increased to about three times a volume of the inner tubular member lumen 150'. In some embodiments, this volume ratio optimizes vacuum generation and tissue travel through the inner tubular member lumen 150', and minimizes tissue clogging therein.

Releasing the trigger 126' allows the spring 128' to restore the second end 134' of the trigger 126' to its un-actuated position away from the handle 152. When the trigger 126' is restored to its un-actuated position, the piston 136' is pushed proximally toward the proximal wall of the vacuum generation chamber 138', thereby decreasing the volume of the vacuum generation chamber 138' and increasing the pressure therein, as shown in FIG. 7.

Figure 20:
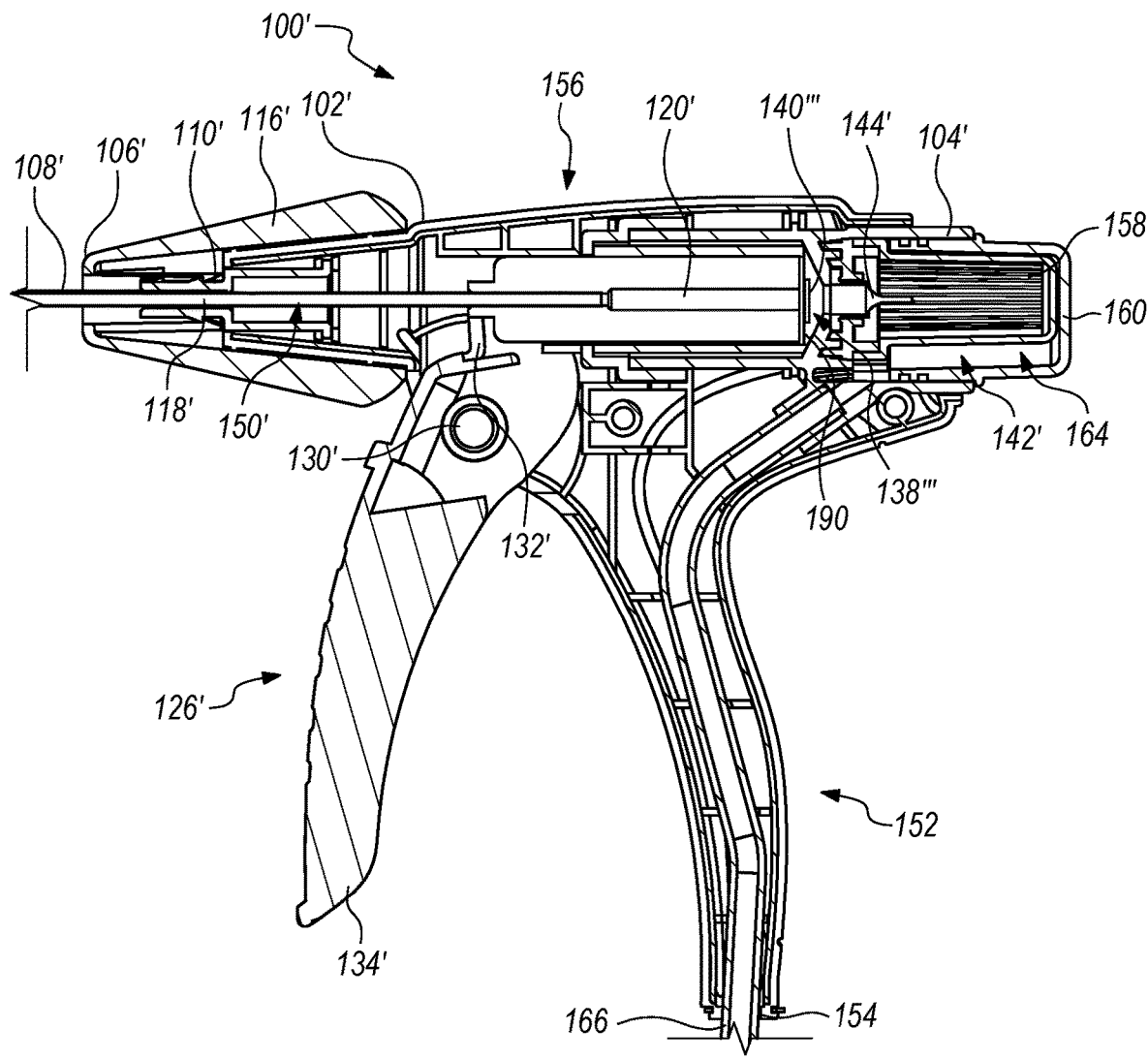
FIGS. 20 and 21 are detailed cross-sectional side views of a fourth embodiment of a tissue removal device constructed according to the teachings of the disclosure showing a bellows, with an actuator of the tissue removal device in un-actuated and actuated states, respectively.
Figure 21:
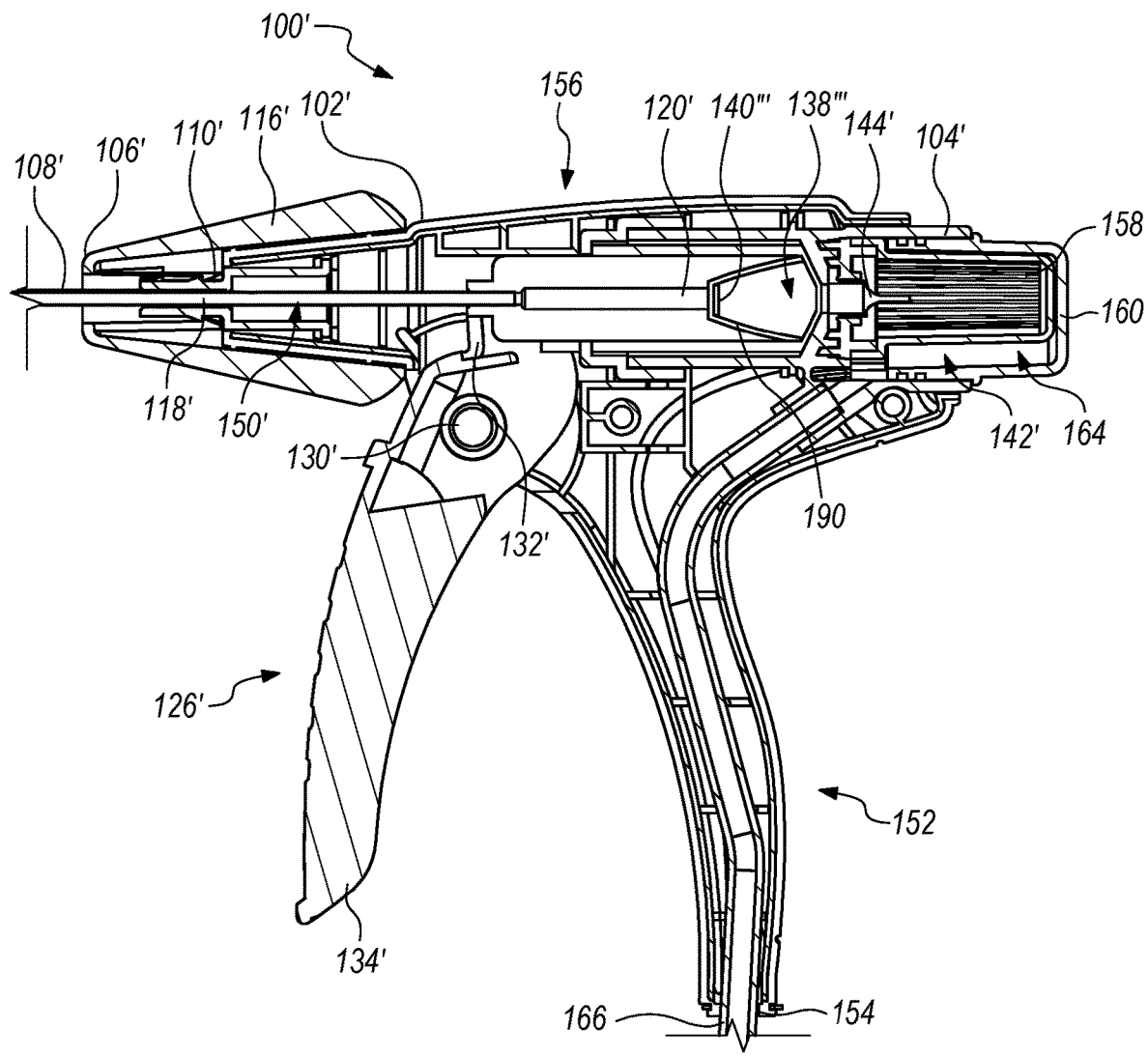

While the tissue removal device 100' depicted in FIGS. 5-14 generates vacuum and pressure with a vacuum generation chamber 138' having a movable piston/plunger 136', other tissue removal devices may incorporate other manual vacuum/pressure generation mechanisms. For instance, some the embodiment depicted in FIGS. 20 and 2 includes a bellows 190 in place of a piston/plunger 136' that forms a wall of the vacuum generation chamber 138' depicted in FIG. 9. The bellows 190 in FIGS. 20 and 21 includes a movable or elastically deformable distal wall 190 in place of a movable piston/plunger. Like the piston/plunger, the distal wall 190 is fluidly coupled to the inner tubular member lumen 150' via a distal one-way valve 140". The movable distal wall 190 is physically coupled to the trigger 126' such that actuating the trigger 126' moves the distal wall 190 distally to increase the volume of the vacuum generation chamber 138" (compare FIGS. 20 and 21) and generate vacuum (i.e., lower pressure) therein. Further, releasing the trigger 126' (which is biased in an un-actuated configuration) moves the distal wall 190 proximally to decrease the volume of the vacuum generation chamber 138" and increase the pressure therein. In the embodiment depicted in FIGS. 20 and 21, the distal wall 190 is elastic (e.g., made from rubber) and the volume of the vacuum generation chamber 138" can be increased and vacuum generated therein by elastically deforming/stretching the rubber distal wall 190 in a distal direction. Further, the elastic restoration of the distal wall 190 can be utilized to drive (partially or completely) longitudinal movement of the inner tubular member 118 and bias the trigger 126' in its un-actuated configuration. Moreover, the distal one-way valve 140" may be a flap valve 140" configured to allow proximally directed fluid flow. Replacing the piston/plunger 136' in FIG. 7-9 with the bellows 190 in FIGS. 20 and 21 eliminates the need for a slidable O-ring assembly to prevent fluid from leaking around the piston/plunger 136', thereby reducing friction and the trigger force needed to actuate the trigger 126'. In other embodiments, the vacuum generation chamber may be replaced and/or supplemented with one or more peristaltic pumps, vane pumps, and rotatory pump.

The proximal end 120' of the inner tubular member 118' may be fluidly coupled to and/or form part of the piston/plunger 136'. The vacuum generation chamber 138' is selectively fluidly coupled to the inner tubular member lumen 150' through a distal one-way valve 140' (e.g., a duck-bill valve). The distal one-way valve 140' may be fluidly coupled to and/or form a part of a proximal end of the piston/plunger 136'. The distal one-way valve 140' is configured to open when vacuum is generated in the vacuum generation chamber 138', thereby allowing severed tissue and/or fluid to be drawn from the inner tubular member lumen 150' into the vacuum generation chamber 138'. The distal one-way valve 140' is also configured to close when pressure is increased in the vacuum generation chamber 138', thereby preventing severed tissue and/or fluid from being pushed from the vacuum generation chamber 138' into the inner tubular member lumen 150'.

In particular, the distal one-way valve 140' is configured to open when the pressure distal of the distal one-way valve 140' (i.e., in the inner tubular member lumen 150') (the "distal pressure") is approximately 40 mm Hg greater than the pressure proximal of the distal one-way valve 140' (i.e., in the vacuum generation chamber 138') (the "proximal pressure"). The distal one-way valve 140' is also configured to remain at least partially open as long as the distal pressure is at least approximately 40 mm Hg greater than the proximal pressure. When the distal pressure is less than approximately 40 mm Hg greater than the proximal pressure (or the proximal pressure is greater than the distal pressure), the distal one-way valve 140' will be closed.

The vacuum generation chamber 138' is also selectively fluidly coupled to a specimen collection chamber 142' through a proximal one-way valve 144' (e.g., a duck-bill valve). The proximal one-way valve 144' may be coupled to or form a part of the body 156 adjacent a proximal end 104' thereof. The proximal one-way valve 144' is configured to open when a pressure is increased in the vacuum generation chamber 138' (i.e., the reverse of the distal one-way valve 140'), thereby allowing severed tissue and/or fluid to be pushed from the vacuum generation chamber 138' into the specimen collection chamber 142'. The proximal one-way valve 144' is also configured to close when vacuum is generated in the vacuum generation chamber 138' (i.e., the reverse of the distal one-way valve 140'), thereby preventing severed tissue and/or fluid (e.g., air) from being drawn from proximal portions of the device 100' (e.g., the specimen collection chamber 142') into the vacuum generation chamber 138'.

In particular, the proximal one-way valve 144' is configured to open when the pressure distal of the proximal one-way valve 144' (i.e., in the vacuum generation chamber 138') (the "distal pressure") is approximately 40 mm Hg greater than the pressure proximal of the proximal one-way valve 144' (i.e., in the specimen collection chamber 142') (the "proximal pressure"). The proximal one-way valve 144' is also configured to remain at least partially open as long as the distal pressure is at least approximately 40 mm Hg greater than the proximal pressure. When the distal pressure is less than approximately 40 mm Hg greater than the proximal pressure (or the proximal pressure is greater than the distal pressure), the proximal one-way valve 144' will be closed.

The tissue removal device 100' also includes a porous tissue trap 158 held in the specimen collection chamber 142' by a tissue trap housing 160. The tissue trap 158 is generally cylindrical with a closed proximal end and an open distal end leading to a tissue trap interior 174. The distal end of the tissue trap 158 is configured to mate with a corresponding flange 176 on the body 156 of the tissue removal device 100', such that excised tissue and fluid entering the specimen collection chamber 142' must enter the tissue trap 158 before the fluid may exit the tissue removal device 100'. The tissue trap 158 has openings 162 formed in the longitudinal surface thereof that collectively form a flow path between the tissue trap interior 176 and a bottom portion 164 of the specimen collection chamber 142'. The openings 162 are size to retain excised tissue in the tissue trap 158 while allowing fluid (e.g., distention fluid) to pass through the tissue trap 158 and into the bottom portion 164 of the specimen collection chamber 142'. In one embodiment, the fluid passes through the openings 162 in the tissue trap 158 by gravity separation. The fluid drains from the bottom portion 164 of the specimen collection chamber 142' through an external connector 166 and outside of the tissue removal device 100'. Outside of the tissue removal device 100', the fluid may collect in a fluid trap (not shown) connected to the external connector 166. Such a fluid trap may be open to atmosphere. The tissue trap 158 may be an integrally formed (i.e., molded from a single piece of material) component, which may be made by machining a block or tube of polymer. Alternatively, the tissue trap 158 may be formed using any other manufacturing method including, but not limited to, 3-D printing.

Figure 11:
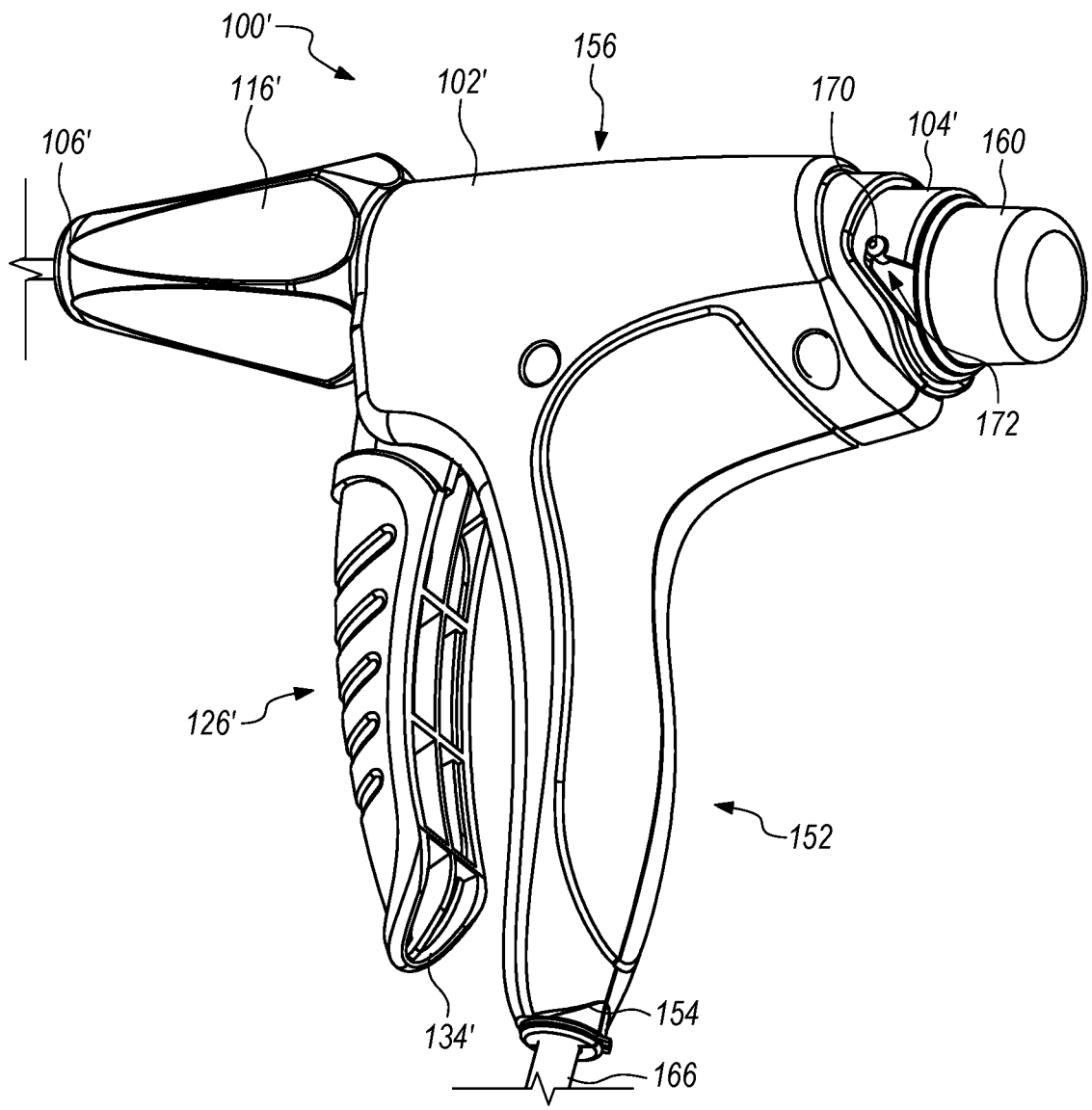
FIGS. 11 and 12 are increasingly detailed perspective views of the tissue removal device depicted in FIG. 5 showing a tissue trap housing, with the actuator of the tissue removal device in an un-actuated state.
Figure 12:
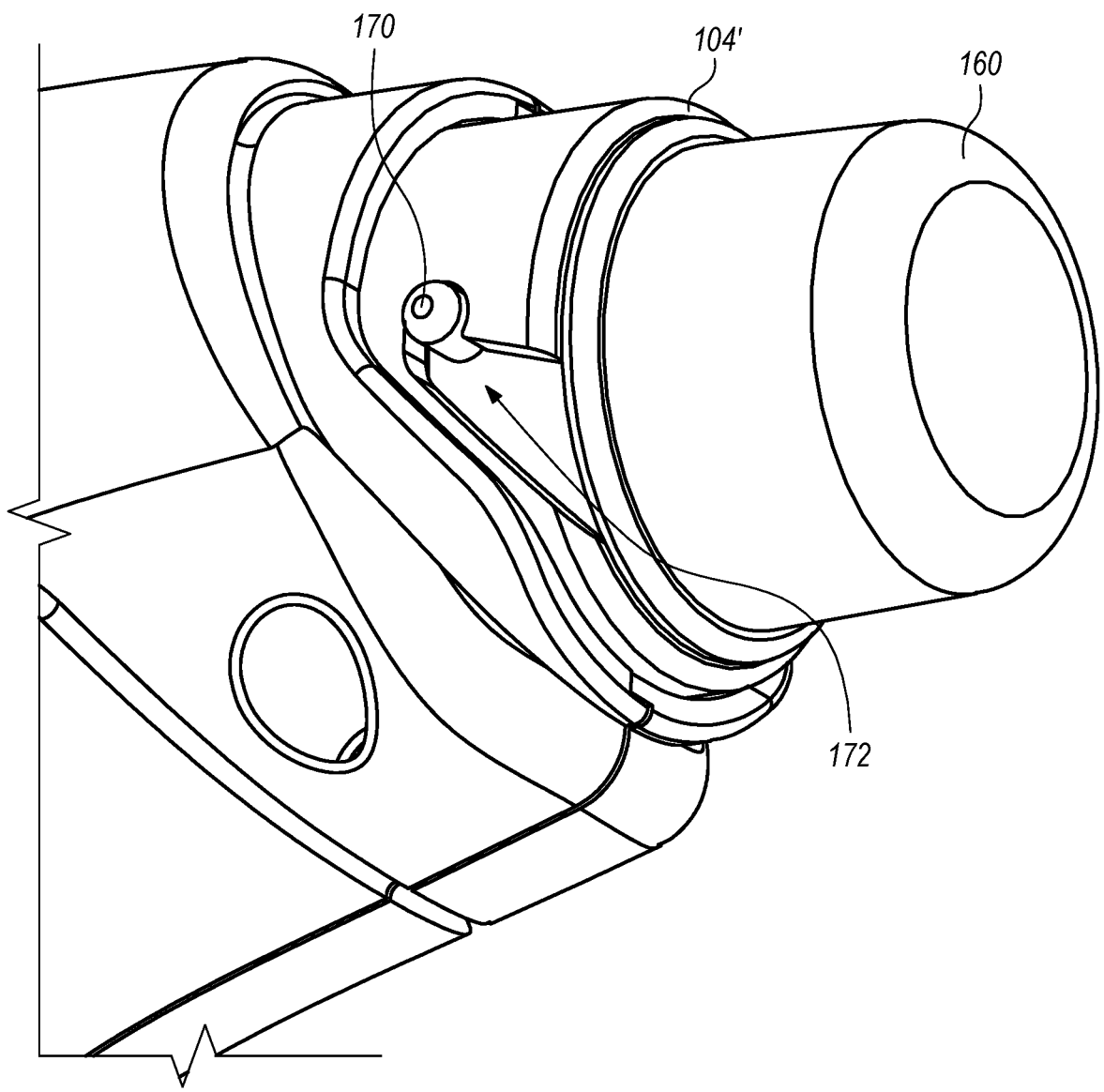

As shown in FIG. 8, the tissue trap housing 160 may include one or more depressions 168 configured to hold one or more O-rings to form a fluid tight seal between the tissue trap housing 160 and the proximal end 104' of the body 156 of the tissue removal device 100'. As shown in FIGS. 11 and 12, the tissue trap housing 160 may include at least one detent 170 configured to cooperate with a wedge-shaped slot 172 to removably lock the tissue trap housing 160 onto the proximal and 104' of the body 156 of the tissue removal device 100'. For instance, the tissue trap housing 160 may be locked with a ¼ turn of the tissue trap housing 160 relative to the housing 102'. After a tissue resection procedure and the excess fluid has drained out of the specimen collection chamber 142', the tissue trap housing 160 can be removed from the proximal and 104' of the body 156 of the tissue removal device 100' by twisting the tissue trap housing 160 counterclockwise to unlock and pulling proximally. After the tissue trap housing 160 has been removed, the tissue trap 158 may remain attached to the proximal end 104' of the body 156 or the tissue trap 158 may be removed with the tissue trap housing 160. In the former case, the tissue trap 158 can be removed from the proximal end 104' of the body 156. In the latter case, the tissue trap 158 can be removed from inside the tissue trap housing 160. Then, the excised tissue can be removed from the tissue trap 158.

While in this embodiment, the pressure differentials are achieved by changing the pressure in the vacuum generation chamber 138', in other embodiments the pressure differentials can also be achieved by changing the pressure in the specimen collection chamber 142' (e.g., using an external vacuum source). In embodiments where the distal and proximal one-way valves 140', 144' are duck-billed valves, the "bills" are facing proximally to allow severed tissue and fluid to travel from the inner tubular member lumen 150' into the vacuum generation chamber 138', and then into the specimen collection chamber 142' and the tissue trap 158. This valve configuration also minimizes backflow of allow severed tissue and fluid from the specimen collection chamber 142' and the tissue trap 158 into the vacuum generation chamber 138', and then into the inner tubular member lumen 150'.

This valve configuration also allows fluid pressure from within the uterus to open both the distal and proximal one-way valves to allow a slow continuous flow of distension fluid out of the uterus through the tissue removal device. In one embodiment, the cracking pressure to open the distal and proximal one-way valves is about 40 mm Hg (difference between distal pressure and proximal pressure). With a 3 L bag of saline hung at an elevation of at least about 0.67 m (about 26.5") to distend a uterus, the distension pressure in the uterus is about 50 mm Hg to 60 mm Hg. Accordingly, the distension pressure is greater than the cracking pressure of the distal and proximal one-way valves, and there is a slow continuous flow of distension fluid through the tissue removal device. The continuous flow of distension fluid eliminates the need to prime the tissue removal device with saline (flush out air bubbles and other material from the flow path), because the pressure differential will automatically cause distension fluid flow and thereby prime the tissue removal device. Further, the continuous flow of distension fluid will draw uterine tissue (e.g., hanging polyps) into the tissue receiving window in the outer tubular member. This drawing of uterine tissue into the tissue receiving window allows the entire cutting stroke of the inner tubular member across the tissue receiving window to be effective to resect tissue at a higher rate (e.g., g/min). Without the continuous fluid flow, vacuum may not be generated until the inner tubular member begins to move across the tissue receiving window, thereby rendering a portion of the cutting stroke ineffective.

The proximal end 120' of the inner tubular member 118' is either physically coupled to or forms part of the piston/plunger 136'. Accordingly, actuating the trigger 126' also moves the inner tubular member 118' longitudinally/axially within the outer tubular member 108'. The distance covered by the inner tubular member 118' during actuating the trigger 126' is greater than the length of the tissue receiving window 114' in the outer tubular member 108'. Actuating the trigger 126' rotates the trigger 126' about the pinned connection 130', and moves the inner tubular member 118' relative to the outer tubular member 108'. In particular, actuating the second end 134' of the trigger 126' toward the handle 152 causes the inner tubular member 118' to be pushed distally within the outer tubular member 108', as shown in FIGS. 9 and 14. Distal movement of the inner tubular member 118' within the outer tubular member 108' moves the cutting edge 124' at the distal end 122' of the inner tubular member 118' across the tissue receiving window 114', thereby severing any tissue prolapsing through the tissue receiving window 114', as shown in FIG. 14 (without the tissue). The tissue removal device 100' is configured such that the vacuum generated in the vacuum generation chamber 138' by actuating the trigger 126' draws tissue into the tissue receiving window 114' before the cutting edge 124' severs the tissue. The device 100' is also configured such that the vacuum generated in the vacuum generation chamber 138' by actuating the trigger 126' also draws severed tissue from the inner tubular member lumen 150' into the vacuum generation chamber 138' through the open distal one-way valve 140' (when there is low pressure in the vacuum generation chamber 138'). The device 100' is further configured such that sufficient vacuum to pull tissue into the tissue receiving window and to pull severed tissue into the vacuum generation chamber 138' is created within the vacuum generation chamber 138' with a single squeeze of the trigger 126'.

Releasing the trigger 126' allows the spring 128' to restore the trigger 126' to its un-actuated position with the second end 134' away from the handle 152. When the trigger 126' is restored to its un-actuated position, the inner tubular member 118' is pulled proximally within the outer tubular member 108', as shown in FIGS. 7 and 13. Proximal movement of the inner tubular member 118' within the outer tubular member 108' opens the tissue receiving opening as shown in FIG. 13. The tissue removal device 100' is configured such that the pressure generated in the vacuum generation chamber 138' by (e.g., the spring 128') restoring the trigger 126' to its un-actuated position pushes severed tissue from the vacuum generation chamber 138' into the specimen collection chamber 142' and the tissue trap 158 before the proximally traveling piston/plunger 136' reduces volume of the vacuum generation chamber 138' to less than the volume of the severed tissue. The device 100' is also configured such that sufficient pressure to push severed tissue into the specimen collection chamber 142' and the tissue trap 158 is created within the vacuum generation chamber 138' with a single restoration of the trigger 126' (e.g., by the spring 128').

As described above, each time the trigger 126' is actuated/squeezed, vacuum is created by the distally moving piston 136' in the vacuum generation chamber 138' and immediately applied to the tissue through the inner tubular member 118', pulling the tissue into the tissue receiving window 114' (see FIG. 14). Further, each time the trigger 126' is actuated/squeezed, the cutting edge 124' travels distally over the tissue receiving window 114', severing tissue prolapsing therethrough. Moreover, the vacuum generated by each trigger 126' actuation/squeeze also opens the distal one-way valve 140' and draws severed tissue (either from the current or a previous stroke) from the inner tubular member lumen 150' into the vacuum generation chamber 138'.

Similarly, each time the spring 128' restores the trigger 126' to its un-actuated position, pressure is created by the proximally moving piston 136' in the vacuum generation chamber 138'. The pressure in the vacuum generation chamber 138' closes the distal one-way valve 140' and opens the proximal one-way valve 144' due to the respective pressure differentials as described above. The pressure in the vacuum generation chamber 138' also pushes the severed tissue (if any) and fluid therein through the open proximal one-way valve 144', and into the specimen collection chamber 142' and the tissue trap 158. As a result, any tissue or fluid (including air) drawn into the device 100' by the vacuum during trigger 126' actuation is off-set by an equal volume of tissue and/or fluid that is ejected into the specimen collection chamber 142' and the tissue trap 158 (which may have a pressure relief valve to prevent build-up of pressure in the device 100' during restoration of trigger '126). Alternatively or additionally, the specimen collection chamber 142' may be coupled by the external connector 166 to atmosphere outside of the tissue removal device 100'. In some embodiments, the external connector 166 may be coupled to an external vacuum source (not shown). In such embodiments, a valve (not shown) may selectively couple the external connection 166 to the external vacuum source such as a pump or a syringe. An example of such a valve may be a pinch valve with the external connector 166 passing therethrough. The external vacuum may generate a pressure differential that overrides and opens both the proximal and distal one-way valves 140', 144'.

Further, each time the trigger 126' is restored, the cutting edge 124' travels proximally over the tissue receiving window 114', opening the tissue receiving window 114' by moving the inner tubular member 118' previously blocking the window 114' proximally away from the window 114' (see FIG. 13). As such, repeatedly actuating the trigger 126' of the tissue removal device 100' efficiently severs tissue, and moves the severed tissue, using vacuum and pressure from the vacuum generation chamber 138', through the device 100' and into the specimen collection chamber 142' and the tissue trap 158. At the completion of a tissue removal procedure, the specimen collection chamber 142' and the tissue trap 158 with the severed tissue therein, can be removed from the device 100'. In other embodiments, each time the trigger 126' is actuated/squeezed, the inner tubular member 118' and its cutting edge 124' are also rotated to facilitate tissue cutting along with the axial reciprocation. For instance, the tissue removal device can include a cam and cam follower (neither shown in FIGS. 5-14) or other components to transfer the actuation motion to rotation of the cutting edge 124' of the inner tubular member 118'. An embodiment with a rotating inner tubular member is described below in FIGS. 17-19 and described below.

Figure 15:
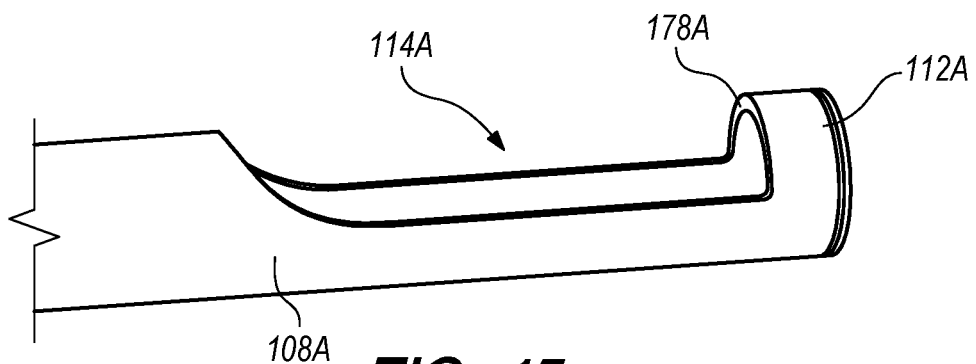
FIGS. 15 and 16 are detailed perspective views of distal ends of the outer tubular members of tissue removal devices according to two embodiments.
Figure 16:
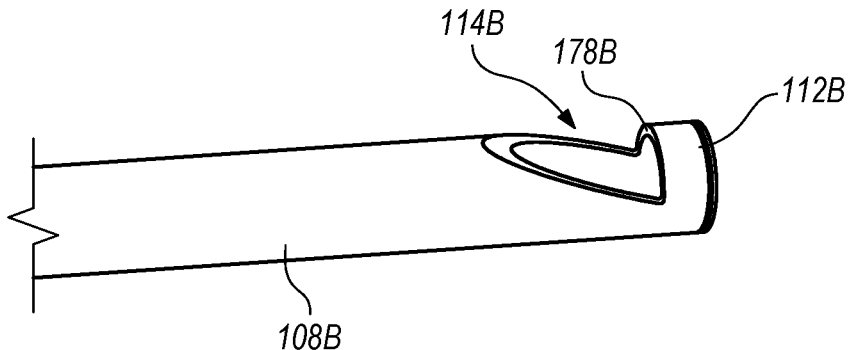

FIGS. 15 and 16 depict two embodiments of distal ends 112A, 112B of respective outer tubular members 108A, 108B that are configured to acquire tissue (e.g., endometrial tissue) using the respective tissue removal devices connected thereto. The distal ends 112A, 112B depicted in FIGS. 15 and 16 can form parts of the tissue removal devices 100, 100' depicted in FIGS. 1-4 and 5-14, respectively, or other tissue removal devices having features similar to features of the tissue removal devices 100, 100'.

Each of the distal ends 112A, 112B includes an edge 178A, 178B at respective distal ends of respective tissue receiving windows 114A, 114B. The edges 178A, 178B are substantially orthogonal to the longitudinal axes of the respective outer tubular members 108A, 108B. Accordingly, when the outer tubular members 108A, 108B are dragged across a tissue surface (e.g., the endometrium), tissue can enter the respective tissue receiving windows 114A, 114B and collect therein as the tissue is scraped by the respective edges 178A, 178B. After the tissue enters the respective tissue receiving windows 114A, 114B, it can be prolapsed by the vacuum generated by the respective tissue removal devices as described above. In some procedures, it may be suitable to collect the tissue using the vacuum with or without cutting by a reciprocating inner tubular member.

In some embodiments, like those described in U.S. Pat. No. 9,060,760, the tissue removal device can operate in a "vacuum mode" and a "cutting mode." The foregoing patent is hereby incorporated by reference into the present application in its entirety as though set forth in full. In such embodiments, like the embodiments described above, the trigger is operatively coupled to the piston/plunger. However, in such embodiments, the trigger may be selectively operatively coupled to the inner tubular member via a yoke, which can be manipulated to select whether the trigger is operatively coupled to or uncoupled from the inner tubular member. For instance, in the cutting mode, the yoke may be placed in a configuration such that the trigger is operatively coupled to the inner tubular member. Consequently, in the cutting mode, actuating the trigger will move both the inner tubular member (to cut tissue prolapsing through the tissue receiving window) and the piston/plunger to deliver vacuum. In the vacuum mode, the yoke may be placed in a configuration such that the tissue is prolapsing through the tissue receiving window while the trigger is operatively uncoupled from the inner tubular member. Consequently, in the vacuum mode, actuating the trigger will move the piston/plunger to generate vacuum, without moving the inner tubular member. In the vacuum mode, the outer tubular member of the tissue removal device can be used as a pipelle (e.g., an endometrial pipelle) to remove tissue (e.g., endometrial tissue) by scraping across a tissue surface. In such embodiments, the distal ends 112A, 112B depicted in FIGS. 15 and 16 can help to remove tissue by scraping.

Figure 17:
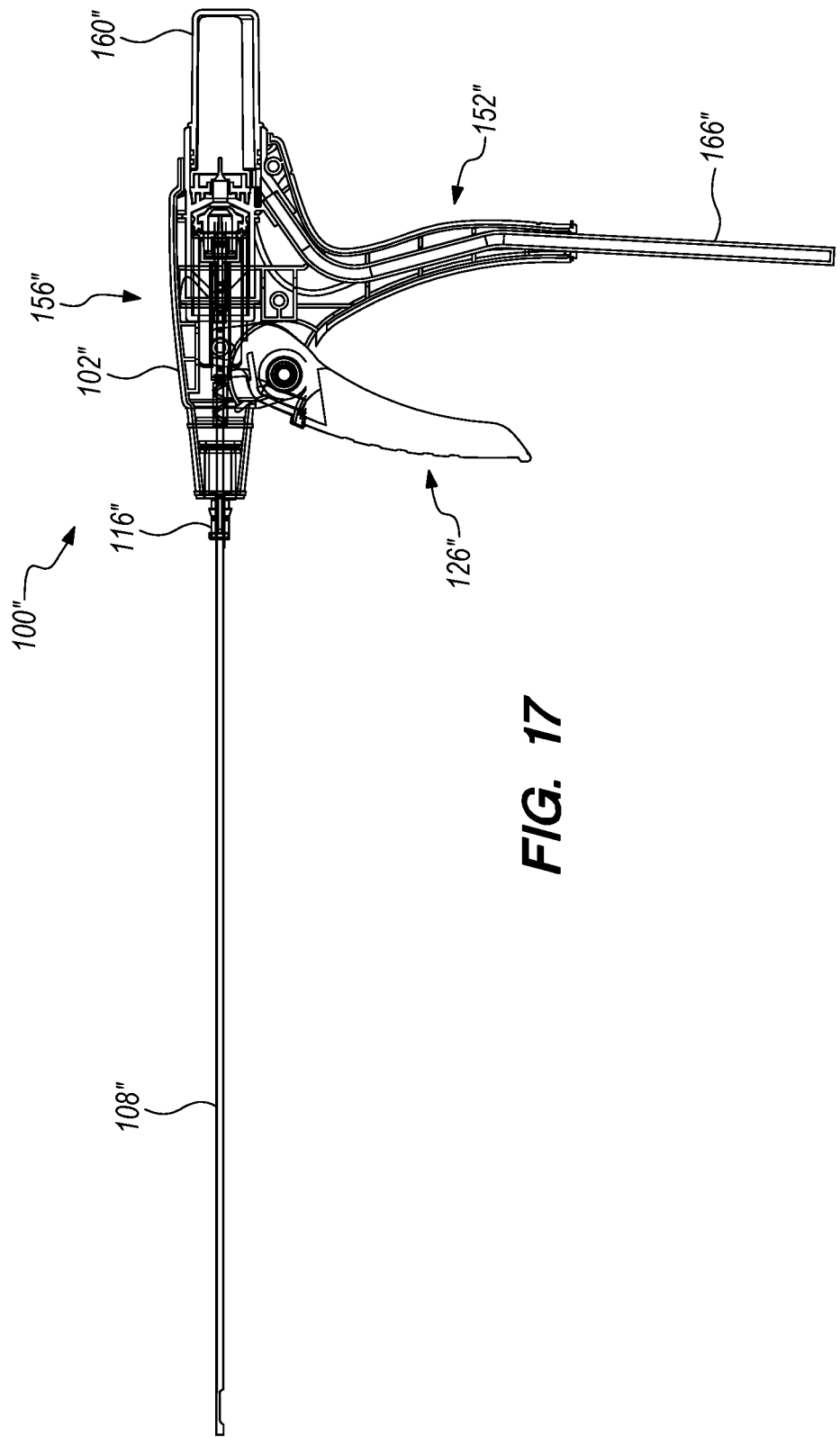
FIGS. 17 and 18 are increasingly detailed cross-sectional side views of a third embodiment of a tissue removal device constructed according to the teachings of the disclosure showing a motion conversion system, with an actuator of the tissue removal device in an un-actuated state.
Figure 18:
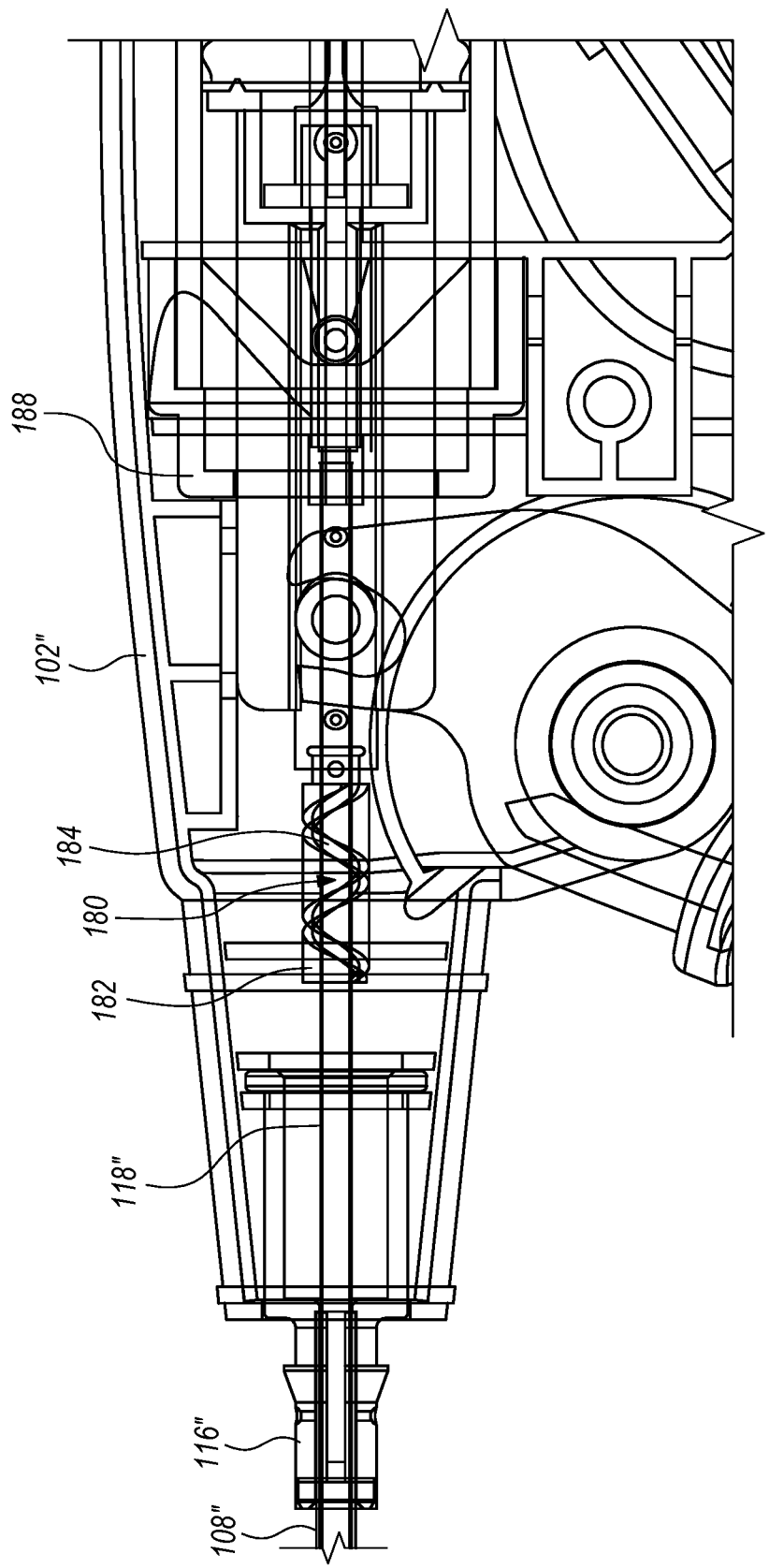
Figure 19:
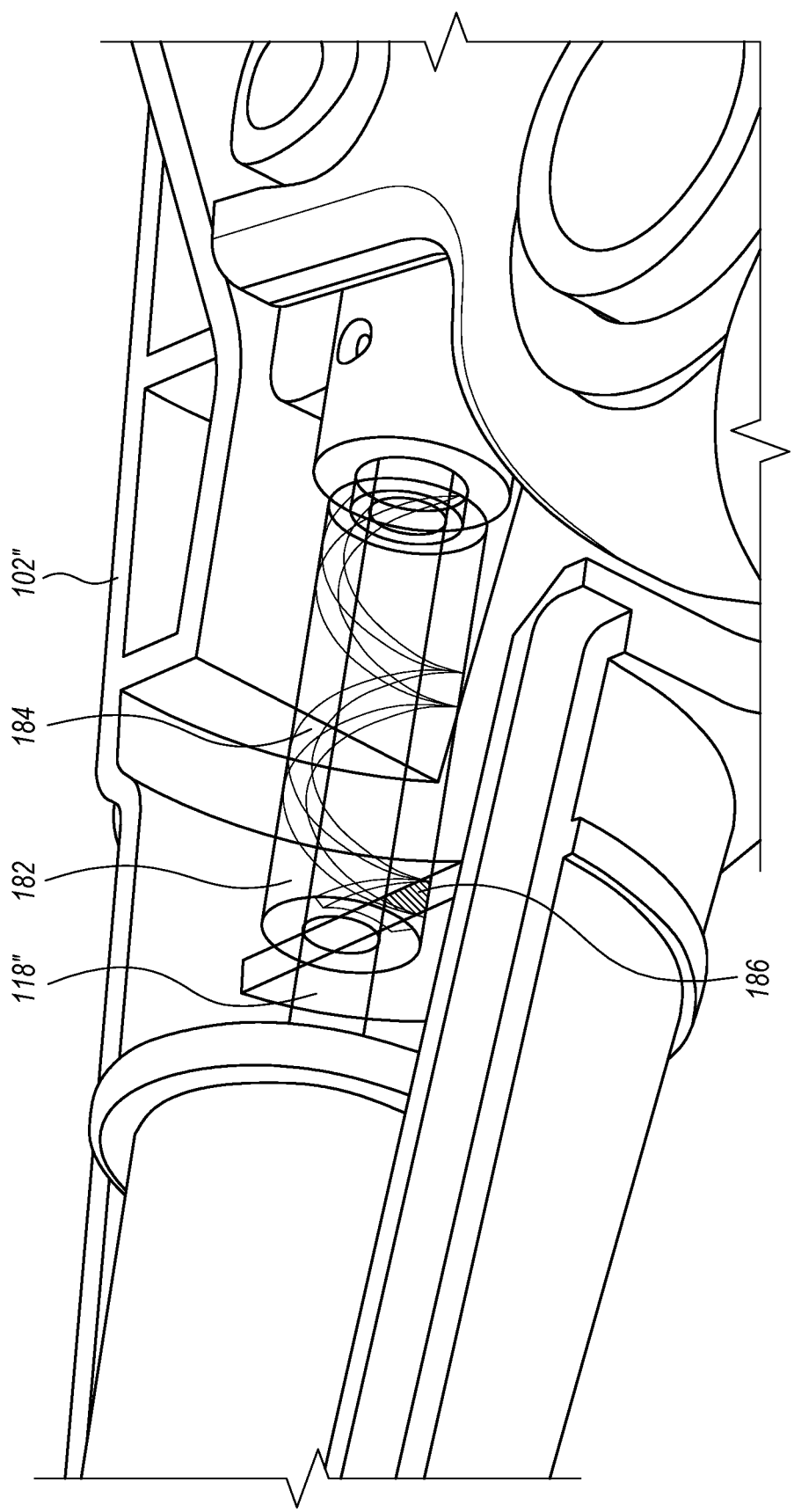
FIG. 19 is a detailed perspective view of the tissue removal device depicted in FIGS. 17 and 18 showing the motion conversion system, with the actuator of the tissue removal device in an un-actuated state.

FIGS. 17-19 depict a tissue removal device 100" according to still another embodiment. In particular, FIGS. 17-19 illustrate a motion conversion system 180 configured to convert linear (e.g., longitudinal/axial) motion of the inner tubular member 118" relative to the housing 102" and the outer tubular member into rotational motion of the inner tubular member 118" relative to the housing 102" and the outer tubular member. The motion conversion system 180 includes an inner tubular member holder 182 physically coupled to the inner tubular member 118" such that the inner tubular member holder 182 and the inner tubular member 118" move both longitudinally and rotationally together. The inner tubular member holder 182 includes a helical groove 184 (i.e., a cam) that spirals around the longitudinal axes of both the inner tubular member holder 182 and the inner tubular member 118". The motion conversion system 180 also includes a cam follower 186 (FIG. 19) physically coupled on an inner surface of the housing 102" such that it is stationary relative to the housing 102". In some embodiments, the cam follower 186 may be formed on the inner surface of the housing 102".

As shown in FIG. 19, the cam follower 186 is disposed in the helical groove 184 and sized and shaped to travel back and forth along the spiral/helix therein. Accordingly, when the inner tubular member 118" moves distally (driven by the trigger to cut tissue prolapsing through the tissue receiving window), the interaction between the helical groove 184 in the inner tubular member holder 182 and the cam follower 186 causes the inner tubular member holder 182 and the inner tubular member 118" coupled thereto to rotate relative to the housing 102" and the outer tubular member. The inner tubular member 118" may be rotatably supported by a barrel 188 portion of the housing 102". Rotation of the inner tubular member 118" also rotates the cutting edge 124 located at a distal end thereof (see FIGS. 3, 4, 13 and 14). Rotating the cutting edge 124 while advancing same over prolapsing tissue increases the efficiency with which the cutting edge 124 severs the tissue. This increased cutting efficiency particularly benefits cutting of more fibrous tissue using a cutting instead of a shearing mechanism. In some embodiments, the In the embodiment depicted in FIG. 19, translating the inner tubular member holder 182 from a proximal most position to a distal most position will rotate the inner tubular member 118" approximately twice. Other embodiments may have different helical grooves that result in different numbers of rotations per stroke. For instance, if the inner tubular member holder is configured to translate only a portion of its length per stroke, the motion conversion system may generate half a rotation per stroke.

In some embodiments, the piston may rotate along with the inner tubular member. In other embodiments, the inner tubular member may be longitudinally coupled to the piston, but free to rotate relative to the piston.

The motion conversion system 180 depicted in FIGS. 17-19 and described above can be used with many embodiments of tissue removal devices including, but not limited to, those depicted in FIGS. 1-4 and 5-14. While the motion conversion system 180 depicted in FIGS. 17-19 include a helical groove 184 coupled to an inner tubular member 118" and a cam follower 186 coupled to a housing 102", other motion conversion systems may have alternative mechanisms for converting linear motion to rotation. For instance, an alternative motion conversion system may include a helical groove coupled to a housing and a cam following coupled to an inner tubular member.

*Although this disclosure has been provided in the context of certain embodiments and examples, it will be understood by those skilled in the art that the disclosure extends beyond the specifically disclosed embodiments to other alternative embodiments and/or uses of the embodiments and obvious modifications and equivalents thereof. Additionally, the skilled artisan will recognize that any of the above-described methods can be carried out using any appropriate apparatus. Further, the disclosure herein of any particular feature, aspect, method, property, characteristic, quality, attribute, element, or the like in connection with an embodiment can be used in all other embodiments set forth herein. Thus, it is intended that the scope of the present inventions disclosed herein should not be limited to the illustrated and/or described embodiments. It will be understood by those skilled in the art that various changes and modifications may be made (e.g., the dimensions of various parts) without departing from the scope of the disclosed inventions, which is to be defined only by the following claims and their equivalents. The specification and drawings are, accordingly, to be regarded in an illustrative rather than restrictive sense.

The invention claimed is:

1. A tissue removal device for acquiring one or more samples of intrauterine tissue, the tissue removal device comprising:
    a housing;
    an outer tube having a distal portion configured for transcervical insertion into a uterus, the outer tube having an outer tube lumen, a tissue in-take window proximate a closed distal end thereof, and a proximal end coupled to the housing;
    an inner tube slidably disposed within the outer tube lumen, the inner tube having an inner tube lumen extending from an open inner tube distal end to an inner tube proximal end, wherein the open inner tube distal end severs intrauterine tissue extending through the tissue in-take window in the outer tube when the inner tube moves from a window-open position to a window-closed position;
    an inner tube holder disposed around and coupled to a portion of the inner tube, the inner tube holder defining a helical groove on an outer surface thereof;
    a cam follower formed on an inner surface of the housing, wherein the cam follower is disposed in the helical groove on the outer surface of the inner tube holder, the helical groove and cam follower being configured such that longitudinal movement of the inner tube relative to the housing causes rotational movement of the inner tube relative to the housing; and
    a manual actuator moveably coupled to the housing and operatively coupled to the inner tube such that moving the manual actuator toward the housing moves the inner tube and the inner tube holder longitudinally relative to the housing, thereby moving the helical groove on the outer surface of the inner tube holder over the cam follower causing rotation of the inner tube holder and the inner tube relative to the housing.

2. The tissue removal device of claim 1, wherein the open inner tube distal end comprises an annular cutting edge.

3. The tissue removal device of claim 1, wherein the housing defines a cylindrical portion configured to support the inner tube.

4. The tissue removal device of claim 1, wherein the helical groove and the cam follower are configured such that translating the inner tube holder from a proximal most position to a distal most position relative to the housing rotates the inner tube approximately twice around a longitudinal axis of the inner tube.

5. The tissue removal device of claim 1, further comprising a spring operatively coupled to the inner tube, wherein movement of the manual actuator relative to the housing compresses the spring.

6. The tissue removal device of claim 1, further comprising an external connector configured to pneumatically couple the device to an external vacuum source.

7. The tissue removal device of claim 1, further comprising a specimen collection chamber in communication with the inner tube lumen.

8. The tissue removal device of claim 1, further comprising a body disposed around and coupled to the inner tube proximal of the inner tube holder, wherein the manual actuator is operatively coupled to the body such that moving the manual actuator toward the housing moves the body longitudinally relative to the housing, thereby moving the respective inner tube and inner tube holder longitudinally relative to the housing.

9. A tissue removal device for acquiring one or more samples of intrauterine tissue, the tissue removal device comprising:
    a housing;
    an outer tube having a distal portion configured for transcervical insertion into a uterus, the outer tube having an outer tube lumen, a tissue in-take window proximate a closed distal end thereof, and a proximal end coupled to the housing;
    an inner tube slidably disposed within the outer tube lumen, the inner tube having an inner tube lumen extending from an open inner tube distal end to an inner tube proximal end, wherein the open inner tube distal end severs intrauterine tissue extending through the tissue in-take window in the outer tube when the inner tube moves from a window open-position to a window-closed position;
    a spring operatively coupled to the inner tube;

an inner tube holder disposed around and coupled to a portion of the inner tube, the inner tube holder defining a helical groove on an outer surface thereof;
a body disposed around and coupled to the inner tube proximal of the inner tube holder;
a cam follower formed on an inner surface of the housing, wherein the cam follower is disposed in the helical groove on the outer surface of the inner tube holder, the helical groove and cam follower being configured such that longitudinal movement of the inner tube relative to the housing causes rotational movement of the inner tube relative to the housing; and
a manual actuator moveably coupled to the housing and operatively coupled to the body such that moving the manual actuator toward the housing moves the respective body, inner tube, and inner tube holder longitudinally relative to the housing, thereby moving the helical groove over the cam follower on the inner surface of the housing causing rotation of the respective-inner tube holder and the inner tube relative to the housing.

10. The tissue removal device of claim 9, wherein the housing defines a cylindrical portion configured to support the inner tube.

11. The tissue removal device of claim 9, wherein the helical groove and the cam follower are configured such that translating the inner tube holder from a proximal most position to a distal most position relative to the housing rotates the inner tube approximately twice around a longitudinal axis of the inner tube.

12. The tissue removal device of claim 9, wherein movement of the manual actuator relative to the housing compresses the spring.

13. The tissue removal device of claim 9, wherein the manual actuator is operatively coupled to the body such that moving the manual actuator toward the housing moves the body longitudinally relative to the housing, thereby moving the respective inner tube and inner tube holder longitudinally relative to the housing.

* * * * *